(12) United States Patent
Soliman et al.

(10) Patent No.: US 7,788,037 B2
(45) Date of Patent: Aug. 31, 2010

(54) METHOD AND SYSTEM FOR DETERMINING FORMATION PROPERTIES BASED ON FRACTURE TREATMENT

(75) Inventors: Mohamed Soliman, Plano, TX (US); David Adams, Katy, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 11/031,874

(22) Filed: Jan. 8, 2005

(65) Prior Publication Data

US 2006/0155473 A1 Jul. 13, 2006

(51) Int. Cl.
*G01N 15/08* (2006.01)
(52) U.S. Cl. ....................................................... 702/12
(58) Field of Classification Search ............... 702/1–14; 166/250.1; 703/10; 175/45
See application file for complete search history.

(56) References Cited

U.S. PATENT DOCUMENTS

| | | | | |
|---|---|---|---|---|
| 4,372,380 | A * | 2/1983 | Smith et al. | 166/250.1 |
| 4,442,710 | A * | 4/1984 | Meng | 73/152.31 |
| 4,549,608 | A * | 10/1985 | Stowe et al. | 166/280.1 |
| 4,797,821 | A | 1/1989 | Petak et al. | 364/422 |
| 4,828,028 | A | 5/1989 | Soliman et al. | 166/250 |
| 4,836,280 | A | 6/1989 | Soliman | 166/250 |
| 5,005,643 | A | 4/1991 | Soliman et al. | 166/250 |
| 5,050,674 | A * | 9/1991 | Soliman et al. | 166/250.1 |
| 5,111,881 | A | 5/1992 | Soliman et al. | 166/250 |
| 5,183,109 | A * | 2/1993 | Poulsen | 166/250.1 |
| 5,275,041 | A * | 1/1994 | Poulsen | 73/152.31 |
| 5,305,211 | A | 4/1994 | Soliman | 364/422 |
| 6,076,046 | A * | 6/2000 | Vasudevan et al. | 702/12 |
| 6,283,210 | B1 | 9/2001 | Soliman et al. | 166/270 |
| 6,347,283 | B1 | 2/2002 | Soliman et al. | 702/6 |
| 6,364,015 | B1 * | 4/2002 | Upchurch | 166/250.1 |
| 6,619,394 | B2 | 9/2003 | Soliman et al. | 166/249 |
| 6,705,398 | B2 * | 3/2004 | Weng | 166/250.1 |
| 6,719,055 | B2 | 4/2004 | Mese et al. | 166/308 |
| 6,795,773 | B2 | 9/2004 | Soliman et al. | 702/6 |
| 6,959,773 | B2 | 11/2005 | Mese et al. | |
| 6,978,211 | B2 | 12/2005 | Soliman et al. | |
| 6,981,549 | B2 * | 1/2006 | Morales et al. | 166/250.1 |
| 7,089,167 | B2 * | 8/2006 | Poe | 703/10 |
| 7,237,612 | B2 | 7/2007 | Surjaatmadja et al. | |
| 7,267,171 | B2 | 9/2007 | Dusterhoft et al. | |
| 7,343,973 | B2 | 3/2008 | Dusterhoft et al. | |
| 7,431,090 | B2 | 10/2008 | Surjaatmadja et al. | |

(Continued)

OTHER PUBLICATIONS

Mayerhofer, et al, *Pressure Transient Analysis of Fracture Calibration Test*, SPE 26527, published 1993, Society of Petroleum Engineers, pp. 217-230, (presented 68th Annual Technical Conference and Exhibition of the Society of Petroleum Engineers, Houston, TX, Oct. 3-6, 1993.

(Continued)

*Primary Examiner*—Tung S Lau
(74) *Attorney, Agent, or Firm*—Robert A. Kent

(57) ABSTRACT

A method and system for determining formation properties based on a fracture treatment that may include collecting data from a fracture treatment for a well. A flow regime of the fracture treatment is determined based on the data. Formation properties may be determined based on the flow regime and the data.

27 Claims, 24 Drawing Sheets

U.S. PATENT DOCUMENTS

| | | | |
|---|---|---|---|
| 7,445,045 | B2 | 11/2008 | East, Jr. et al. |
| 7,543,635 | B2 | 6/2009 | East et al. |
| 2003/0050758 | A1 | 3/2003 | Soliman et al. ............... 702/6 |
| 2003/0205375 | A1* | 11/2003 | Wright et al. ............ 166/250.1 |
| 2005/0269099 | A1 | 12/2005 | Stegent et al. |
| 2005/0269101 | A1 | 12/2005 | Stegent et al. |
| 2005/0284637 | A1 | 12/2005 | Stegent et al. |
| 2006/0155473 | A1* | 7/2006 | Soliman et al. ............... 702/12 |
| 2006/0201674 | A1 | 9/2006 | Soliman et al. |
| 2007/0272407 | A1 | 11/2007 | Lehman et al. |
| 2008/0083538 | A1 | 4/2008 | Soliman |
| 2009/0125280 | A1 | 5/2009 | Soliman et al. |

OTHER PUBLICATIONS

Barree, et al, *Determination of Pressure Dependent Leakoff and Its Effect on Fracture Geometry, SPE 36424*, published 1996, Society of Petroleum Engineers, Inc., pp. 1-10, (presented 71$^{st}$ Annual Technical Conference and Exhibition, Denver, CO, Oct. 6-9, 1996.

Valko, et al, *Fluid Leakoff Delineation in High-Permeability Fracturing, SPE 37403*, published 1997, Society of Petroleum Engineers, Inc., *SPE Production & Facilities*, May 1999, pp. 135-150, (presented 1997 SPE Production Operations Symposium, Oklahoma City, OK Mar. 9-12).

Nolte, et al, *After-Closure Analysis of Fracture Calibration Tests, SPE 38676*, published 1997, Society of Petroleum Engineers, Inc., pp. 333-348, (presented 1997 SPE Annual Technical Conference and Exhibition, San Antonio, TX, Oct. 5-8).

Barree, et al, *Applications of Pre-Frac Injection/Falloff Tests in Fissured Reservoirs—Field Examples, SPE 39932*, published 1998, Society of Petroleum Engineers, Inc., pp. 277-288, (presented 1998 SPE Rocky Mountain Regional/Low-Permeability Reservoirs Symposium and Exhibition, Denver, CO, Apr. 5-8).

Rollins, et al, *Pressure-Dependent Leakoff in Fracturing—Field Examples from the Haynesville Sand, SPE 39953*, published 1998, Society of Petroleum Engineers, Inc., pp. 433-441, (presented SPE Rocky Mountain Regional Meeting/Low Permeability Reservoirs Symposium and Exhibition, Denver, CO, Apr. 5-8, 1998).

Craig, et al, *Estimating Pore Pressure and Permeability in Massively Stacked Lenticular Reservoirs Using Diagnostic Fracture-Injection Tests, SPE 56600*, published 1999, Society of Petroleum Engineers, Inc., pp. 1-14, (presented 1999 SPE Annual Technical Conference and Exhibition, Houston, TX, Oct. 3-6).

Craig, et al, *Adapting High Permeability Leakoff Analysis to Low Permeability Sands for Estimating Reservoir Engineering Parameters, SPE 60291*, published 2000, Society of Petroleum Engineers, Inc., pp. 1-9, (presented 2000 SPE Rocky Mountain Regional/Low Permeability Reservoirs Symposium, Denver, CO, Mar. 12-15).

Soliman, et al, *Design, Interpretation, and Assessment of Short-Term Pressure-Transient Tests, SPE 90837*, published 2004, Society of Petroleum Engineers, Inc., pp. 1-13, (presented SPE Annual Technical Conference and Exhibition, Houston, TX, Sep. 26-29, 2004).

Abousleiman, et al, *Formation Permeability Determination by Micro or Mini-Hydraulic Fracturing, Journal of Energy Resources Technology*, vol. 116, Jun. 1994, pp. 104-114.

Soliman, et al, *Method Analyzes Pressure for Short Flow Times, Oil and Gas Journal*, Technology, Apr. 30, 1990, pp. 49-54.

Soliman, et al, *Practical Use of Numerical Simulator in Oil Industry*, presented at SPE Bergen Seminar, Bergen, Norway, Apr. 20, 2004, 32 pgs.

Nolte, *Determination of Fracture Parameters from Fracturing Pressure Decline, SPE 8341*, published 1979, American Institute of Mining, Metallurgical, and Petroleum Engineers, Inc. (presented at the Society of Petroleum Engineers Meeting, Las Vegas, NV, Sep. 23-26, 1979), 16 pgs.

Soliman, *Analysis of Buildup Tests With Short Producng Time, SPE 11083*, published *SPE Formation Evaluation*, Aug. 1986, pp. 363-371 (presented 1982 SPE Annual Technical Conference and Exhibition in New Orleans, LA, Sep. 26-29) and *Analysis of Buildup Tests With Short Producing Time, SPE 11083*, published 1982, Society of Petroleum Engineers of AIME, pp. 1-14.

Nolte, *A General Analysis of Fracturing Pressure Decline With Application to Three Models, SPE 12941*, published 1986, Society of Petroleum Engineers, *SPE Formation Evaluation*, Dec. 1986, pp. 571-583.

Tan, et al, *Field Application of Minifracture Analysis To Improve Fracturing Treatment Design, SPE 17463, Revised*, published 1990, Society of Petroleum Engineers, *SPE Production Engineering*, May 1990, pp. 125-132 and *Field Application of Minifrac Analysis To Improve Fracturing Treatment Design, SPE 17463*, published 1988, Society of Petroleum Engineers, pp. 591-612 (presented 1988, SPE California Regional Meeting, Long Beach, Mar. 23-25).

Shlyapobersky, et al, *Field Determination of Fracturing Parameters for Overpressure Calibrated Design of Hydraulic Fracturing, SPE 18195*, published 1988, Society of Petroleum Engineers, pp. 149-164, (presented 63$^{rd}$ Annual Technical Conference and Exhibition of the Society of Petroleum Engineers, Houston, TX, Oct. 2-5, 1988.

Soliman, et al, *Fracturing Aspects of Horizontal Wells, SPE 18542*, published 1990, Society of Petroleum Engineers, *JPT*, Aug. 1990, pp. 966-973 and *On Fracturing Horizontal Wells, SPE 18542*, published 1988, Society of Petroleum Engineers, pp. 193-205, (presented SPE Eastern Regional Meeting, Charleston, WV, Nov. 1-4, 1988).

Nolte, *Fracturing-Pressure Analysis for Nonideal Behavior, SPE 20704*, published 1991, Society of Petroleum Engineers, *JPT*, Feb. 1991, pp. 210-218.

Soliman, et al, *Determination of Fracture Volume and Closure Pressure From Pump-In/Flowback Tests, SPE 21400*, published 1991, Society of Petroleum Engineers, pp. 535-542, (presented SPE Middle East Oil Show, Bahrain, Nov. 16-19, 1991.

Mukherjee, et al, *Extension of Fracture Pressure Decline Curve Analysis to Fissured Formations, SPE 21872*, published 1991, Society of Petroleum Engineers, Inc., pp. 671-685, (presented Rocky Mountain Regional Meeting and Low-Permeability Reservoirs Symposium, Denver, CO, Apr. 15-17, 1991).

Gu, et al, *Formation Permeability Determination Using Impulse-Fracture Injection, SPE 25425*, published 1993, Society of Petroleum Engineers, Inc., pp. 189-201, (presented Production Operations Symposium, Oklahoma City, OK, Mar. 21-23, 1993).

Cleary, M.P., et al., "*Field Implementation of Proppant Slugs to Avoid Premature Screen-Out of Hydraulic Fractures with Adequate Proppant Concentration*," SPE 25892, copyright 1993, Society of Petroleum Engineers, Inc., prepared for presentation at the SPE Rocky Mountain Region/Low Permeability Reservoirs Symposium in Denver, CO, Apr. 12-14, 1993, pp. 493-508.

Hyden, Ron, et al., "*Pump-in/Shutdown Tests Key to Finding Near-Wellbore Restrictions*," SPE 35194, copyright 1996, Society of Petroleum Engineers, Inc., prepared for presentation at the Permian Basin Oil and Gas Recovery Conference, Midland, Texas, Mar. 27-29, 1996, pp. 431-436.

Soliman, M.Y., et al., "*Application of Wavelet Transform to Analysis of Pressure Transient Data*," SPE 71571, copyright 1996, Society of Petroleum Engineers, Inc., prepared for presentation at the 2001 SPE Annual Technical Conference and Exhibition, New Orleans, LA Sep. 30-Oct. 3, 2001, pp. 1-13.

Lee, W.S., "*Study of the Effects of Fluid Rheology on Minifrac Analysis*," SPE 16916, copyright 1987, Society of Petroleum Engineers, prepared for presentation at the 62$^{nd}$ Annual Technical Conference and Exhibition of the Society of Petroleum Engineers, Dallas, Texas, Sep. 27-30, 1987, pp. 377-386.

Soliman, M.Y., "*Technique for Considering Fluid Compressibility and Temperature Changes in Mini-Frac Analysis*," SPE 15370, copyright 1986, Society of Petroleum Engineers, prepared for presentation at the 61$^{st}$ Annual Technical Conference and Exhibition of the Society of Petroleum Engineers, New Orleans, LA, Oct. 5-8, 1986, 11 pages.

Perkins, T.K., et al., "*Widths of Hydraulic Fractures*," *Journal of Petroleum Technology*, Sep. 1961, pp. 937-949.

Khristianovic, S.A., et al., "*Formation of Vertical Fractures by Means of Highly Viscous Liquid*," Proceedings Fourth World Petroleum Congress, Rome, Section II/T.O.P., Paper 3, Academy of Sciences, Moscow, USSR, pp. 579-586, 1955.

Cinco, Heber L., et al., "*Transient Pressure Behavior for a Well with a Finite-Conductivity Vertical Fracture*," Society of Petroleum Engineers Journal, Aug. 1978, pp. 253-264.

Lee, W.S., "*Mini-Frac Analysis Based on Ellipsoidal Geometry*," SPE 15369, copyright 1986, Society of Petroleum Engineers, prepared for presentation at the 61$^{st}$ Annual Technical Conference and Exhibition of the Society of Petroleum Engineers, New Orleans, LA, Oct. 5-8, 1986, pp. 1-8.

* cited by examiner

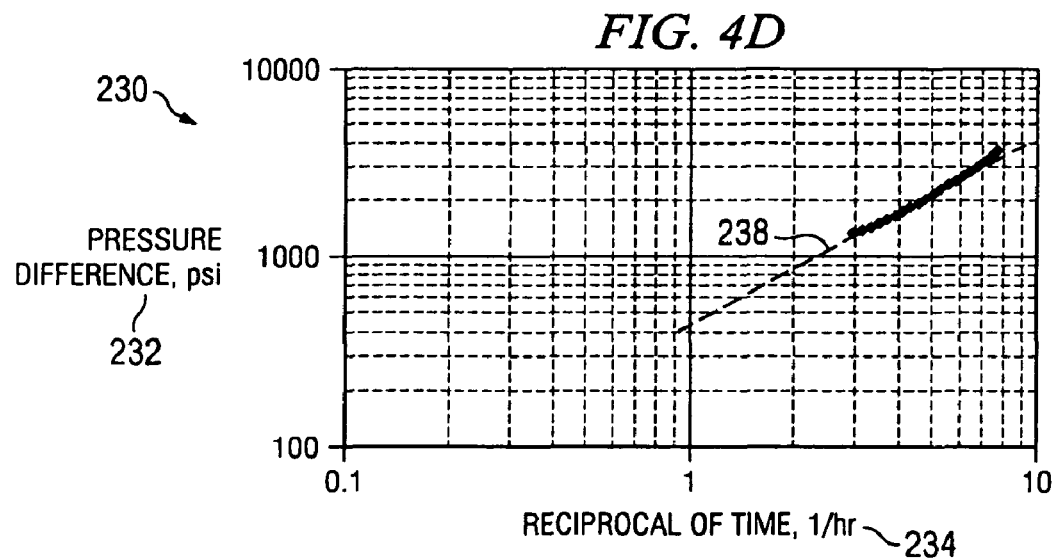
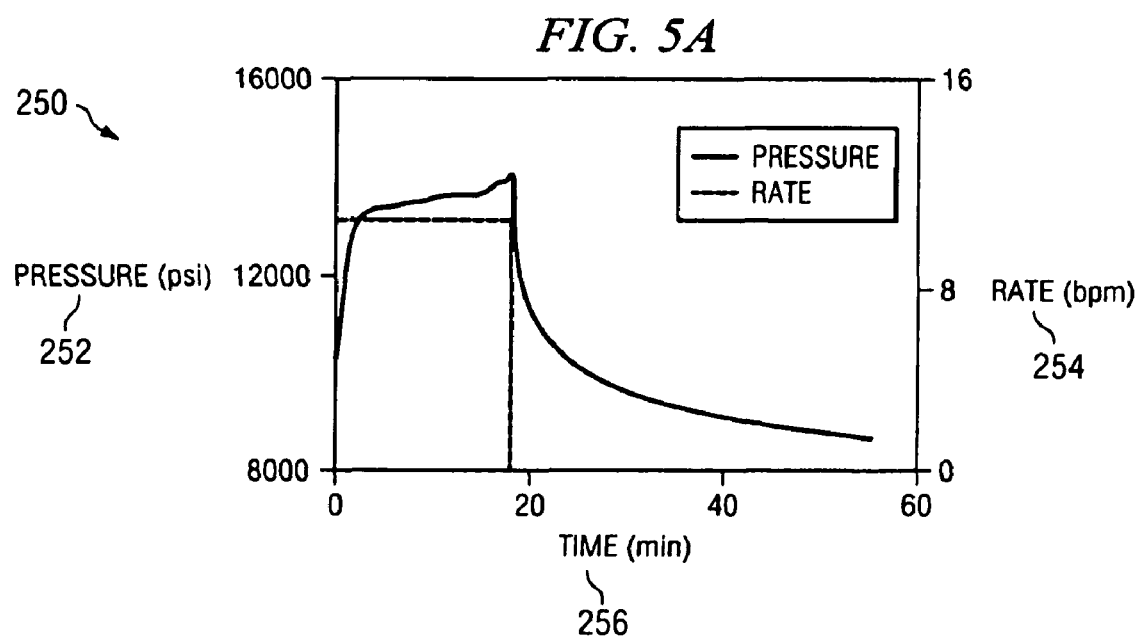

US 7,788,037 B2

METHOD AND SYSTEM FOR DETERMINING FORMATION PROPERTIES BASED ON FRACTURE TREATMENT

TECHNICAL FIELD

Fracture stimulation of a well, and more particularly to a method and system for determining formation properties based on a fracture treatment.

BACKGROUND

Oil and gas wells produce oil, gas and/or byproducts from underground reservoirs. Oil and gas reservoirs are formations of rock containing oil and/or gas. The type and properties of the rock may vary by reservoir and also within reservoirs. For example, the porosity and permeability of a reservoir rock may vary from reservoir to reservoir and from well to well in a reservoir. The porosity is the percentage of core volume, or void space, within the reservoir rock that can contain fluids. The permeability is an estimate of the reservoir rock's ability to flow or transmit fluids.

Oil and gas production from a well may be stimulated by fracture, acid or other production enhancement treatment. In a fracture treatment, fluids are pumped downhole under high pressure to artificially fracture the reservoir rock in order to increase permeability and production. First, a pad, which is fracture fluids without proppants is pumped down the well until formation breakdown. Then, the fracturing fluid with proppants is pumped downhole to hold the fractures open after pumping stops. At the end of the fracture treatment, a clear fluid flush may be pumped down the well to clean the well of proppants.

An initial, or minifracture, test may be performed before a regular fracture stimulation treatment to calculate formation and fracture properties. Recently, analysis techniques were extended to the after-closure period. In this analysis, the after-closure data are analyzed to calculate formation permeability and reservoir pressure. This calculation hypothesizes the existence of either pseudo-radial or linear flow during the after-closure period.

SUMMARY

A method and system for determining fracture properties are provided. In accordance with one embodiment, a method for determining fracture properties may include collecting data from a fracture treatment for a well. A flow regime from the fracture treatment is determined based on the data. In a specific embodiment, formation properties may be determined based on the flow regime and the data.

Technical advantages of the method and system may include a more generalized, simplified, and/or accurate technique for determining fracture and formation properties from a fracture treatment. For example, the flow regime dominating the post-closure period of a fracture treatment may be determined based on measured data rather than general assumptions and/or equations. Accordingly, the type of residual fracture may be determined. Reservoir properties such as permeability and pressure may then be determined based on the specific flow regime.

Another technical advantage of one or more embodiments may include an improved full, or other subsequent fracture treatment following a minifracture test or other initial fracture treatment. For example, fracture fluids and proppants as well as the duration of pad, proppant, and flush stages may be optimized or otherwise enhanced based on reservoir permeability and pressure determined from an initial fracture treatment.

Details of the one or more embodiments of the disclosure are set forth in the accompanying drawings in the description below. Other features, objects, and advantages of some of the embodiments will be apparent from the description and drawings, and from the claims. Some, all, or none of the embodiments may include advantages described herein.

DESCRIPTION OF DRAWINGS

FIGS. 4A-D illustrate exemplary graphs for determining formation properties from an exemplary fracture treatment having a post-closure pseudo-radial flow regime;

FIGS. 5A-5D illustrate exemplary graphs for determining formation properties from an exemplary fracture treatment having a post-closure bilinear flow regime of pressure functions for various flow regimes.

DETAILED DESCRIPTION

Figure 1:
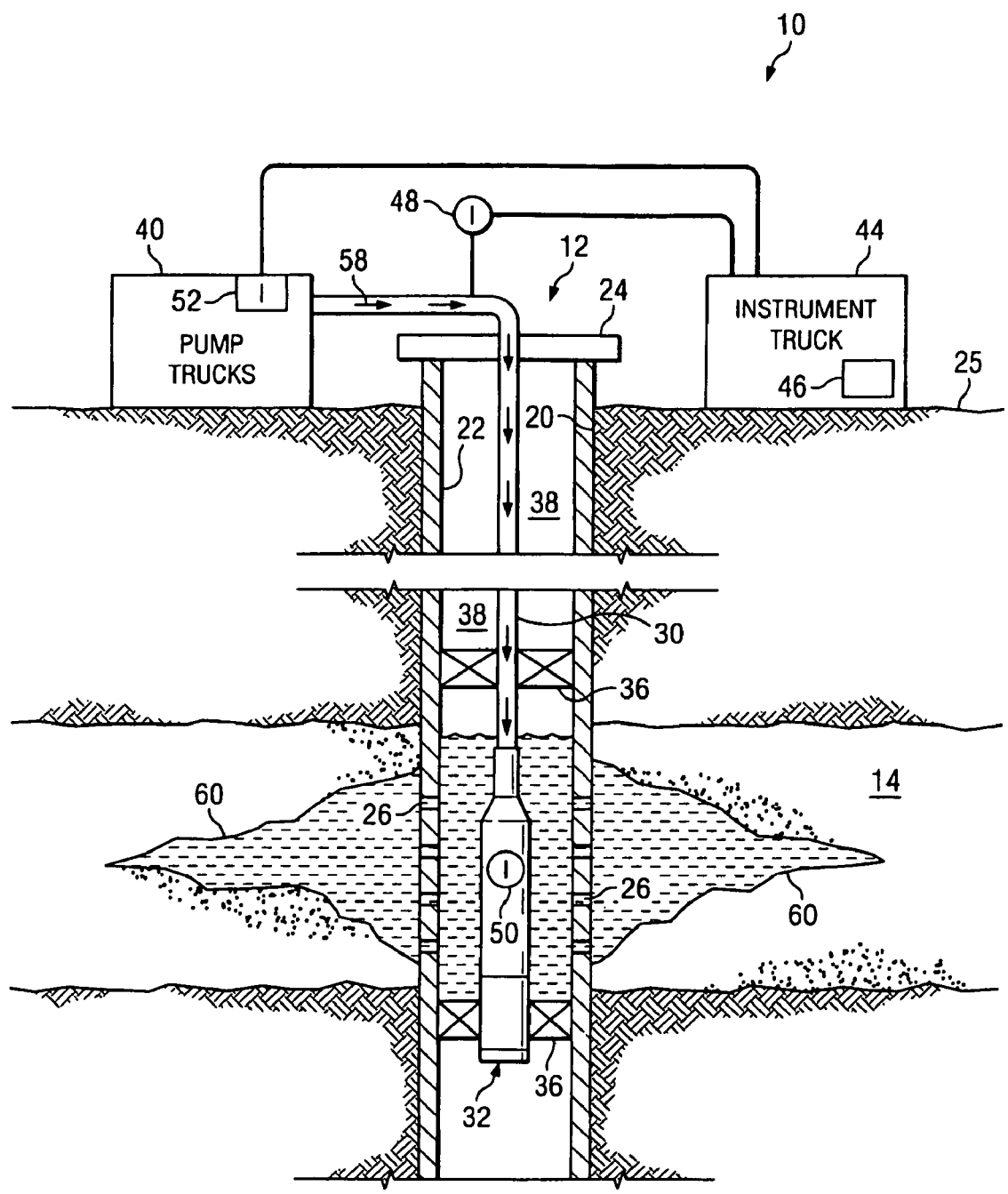
FIG. 1 illustrates one embodiment of a fracture treatment for a well.

FIG. 1 illustrates one embodiment of a fracture treatment 10 for a well 12. The well 12 may be an oil and gas well intersecting a reservoir 14. In this embodiment, the reservoir 14 comprises an underground formation of rock containing oil and/or gas. The well 12 may in other embodiments, intersect other suitable types of reservoirs 14.

The fracture treatment 10 may comprise a mini fracture test treatment or other suitable treatment. In the mini fracture test treatment embodiment, the fracture treatment 10 may be used to determine formation properties and residual fracture properties before a regular or full fracture treatment. The formation properties may comprise, for example, reservoir pressure and formation permeability. The formation permeability is an estimate of the reservoir rock's ability to flow or transmit fluids. In other embodiments, the fracture treatment 10 may comprise a regular or full fracture treatment, a follow-on fracture treatment, a final fracture treatment or other suitable fracture treatment.

The well 12 may include a well bore 20, casing 22 and well head 24. The well bore 20 may be a vertical bore, a horizontal bore, a slanted bore or other deviated bore. The casing 22 may be cemented or otherwise suitably secured in the well bore 12. Perforations 26 may be formed in the casing 22 at the level of the reservoir 14 to allow oil, gas, and by-products to flow into the well 12 and be produced to the surface 25. Perforations 26 may be formed using shape charges, a perforating gun or otherwise.

For the fracture treatment 10, a work string 30 may be disposed in the well bore 20. The work string 30 may be coiled tubing, sectioned pipe or other suitable tubing. A fracturing tool 32 may be coupled to an end of the work string 30. The fracturing tool 32 may comprise a SURGIFRAC or COBRA FRAC tool manufactured by HALLIBURTON or other suitable fracturing tool. Packers 36 may seal an annulus 38 of the well bore 20 above and below the reservoir 14. Packers 36 may be mechanical, fluid inflatable or other suitable packers.

One or more pump trucks 40 may be coupled to the work string 30 at the surface 25. The pump trucks 40 pump fracture fluid 58 down the work string 30 to perform the fracture treatment 10. The fracture fluid 58 may comprise a fluid pad, proppants and/or a flush fluid. The pump trucks 40 may comprise mobile vehicles, equipment such as skids or other suitable structures.

One or more instrument trucks 44 may also be provided at the surface 25. The instrument truck 44 includes a fracture control system 46 for monitoring and controlling the fracture treatment 10. The fracture control system 46 communicates with surface and/or subsurface instruments to monitor and control the fracture treatment 10. In one embodiment, the surface and subsurface instruments may comprise surface sensors 48, down-hole sensors 50 and pump controls 52.

Surface and down-hole sensors 48 and 50 may comprise pressure, rate, temperature and/or other suitable sensors. Pump controls 52 may comprise controls for starting, stopping and/or otherwise controlling pumping as well as controls for selecting and/or otherwise controlling fluids pumped during the fracture treatment 10. Surface and down-hole sensors 48 and 50 as well as pump controls 52 may communicate with the fracture control system 46 over wire-line, wireless or other suitable links. For example, surface sensors 48 and pump controls 52 may communicate with the fracture control system 46 via a wire-line link while down-hole sensors 50 communicate wirelessly to a receiver at the surface 25 that is connected by a wire-line link to the fracture control system 46. In another embodiment, the down-hole sensors 50 may upon retrieval from the well 12 be directly or otherwise connected to fracture control system 46.

In operation, the fracturing tool 32 is coupled to the work string 30 and positioned in the well 12. The packers 36 are set to isolate the reservoir 14. The pump trucks 40 pump fracture fluid 58 down the work string 30 to the fracturing tool 32. The fracture fluid 58 exits the fracturing tool 32 and creates a fracture 60 in the reservoir 14. In a particular embodiment, a fracture fluid 58 may comprise a fluid pad pumped down the well 12 until breakdown of the formation in the reservoir 14. Proppants may then be pumped down-hole followed by a clear fluid flush. The fracture treatment 10 may be otherwise suitably performed.

Figure 2A:
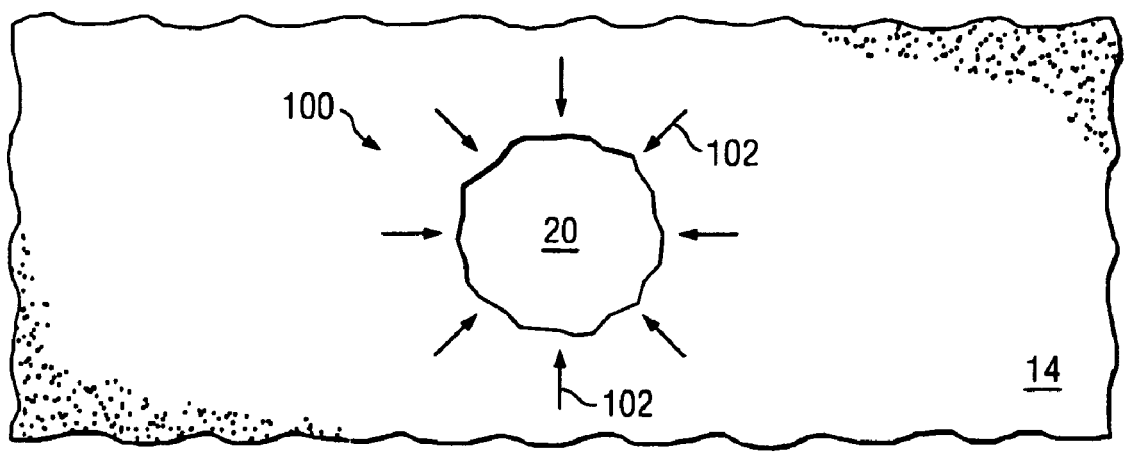
FIGS. 2A-2C illustrate exemplary residual fractures and corresponding flow regimes for the fracture treatment of FIG. 1.
Figure 2B:
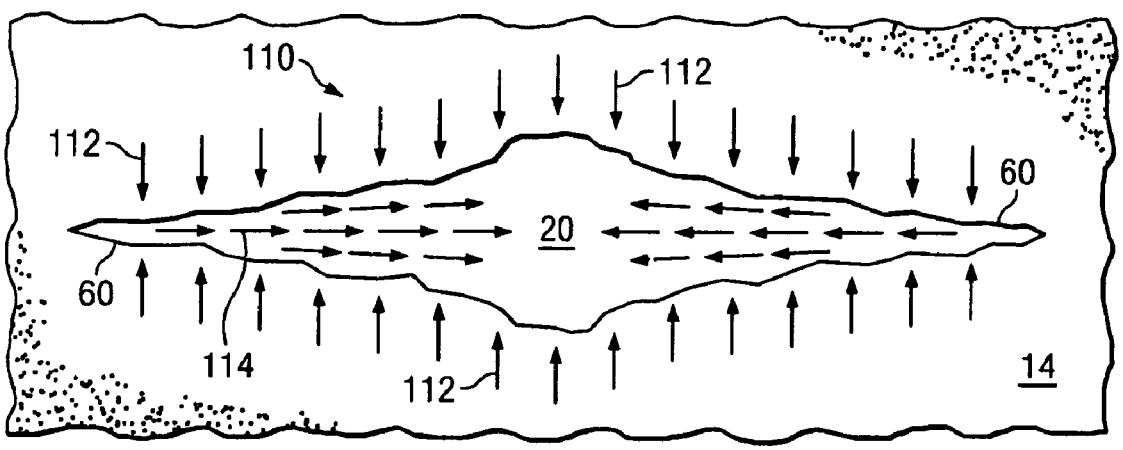
Figure 2C:
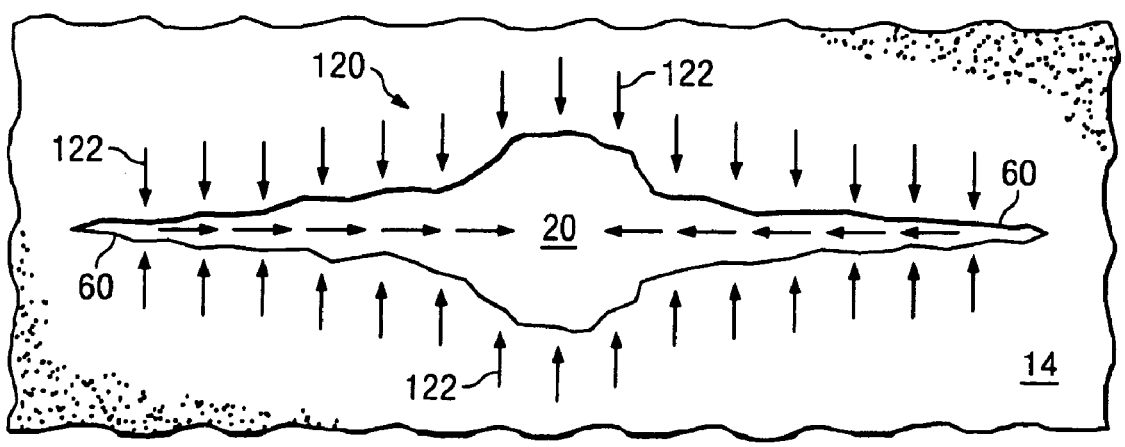

FIGS. 2A-C illustrate a plurality of exemplary flow regimes, not necessarily to scale, formed in the reservoir 14 by the fracture treatment 10. In particular, FIG. 2A illustrates one embodiment of a pseudo-radial flow regime 100. FIG. 2B illustrates one embodiment of a bilinear flow regime 110. FIG. 2C illustrates one embodiment of a linear flow regime 120. Other flow regimes may comprise, for example, a spherical flow regime.

Referring to FIG. 2A, the pseudo-radial flow regime 100 comprises converging streamlines 102. In this embodiment, iso-potential lines are circular and extend radially from the well bore 20. The pseudo-radial flow regime 100 may exist, for example, when the period of the fracture treatment 10 is fairly short and little or no residual fracture conductivity remains after the fracture treatment 10 or after unrealistically long shut in time.

Referring to FIG. 2B, the bilinear flow regime 110 comprises a first set of parallel stream lines 112 and a second set of parallel stream lines 114 perpendicular to the first set of streamlines 112. In this embodiment, the fracture 60 offers some resistance to fluid flow with a significant portion of the total pressure drop occurring in the fracture 60. Thus, the bilinear flow regime 110 is controlled by the pressure drop due to linear flow inside the fracture 60 and the pressure drop due to linear flow in the reservoir 14 surrounding the fracture 60.

Bilinear flow may be present, for example, where the fracture 60 is long or did not completely close, thus maintaining some residual conductivity. The bilinear flow regime 110 may also exist where the fracture treatment 10 comprises an acidized fracture or when release of fragments from the reservoir 14 that act as proppants. As another example, if propagation of the fracture 60 has a plastic component, the fracture 60 may maintain some finite width even at closure and accordingly cause the bilinear flow regime 110.

Referring to FIG. 2C, the linear flow regime 120 comprises parallel stream lines 122. In this embodiment, no appreciable pressure drop occurs inside the fracture 60. The linear flow regime 120 may exist, for example, where the fracture 60 stays open with a high dimensionless conductivity. Dimensionless fracture conductivity may be determined from the product of fracture width and fracture permeability divided by the product of formation permeability and fracture half length. This may occur, for example, where permeability of the reservoir 14 is low and the fracture treatment 10 is conducted with proppants. It may also occur where the fracture 60 stays open for a long period of time.

Figure 3:
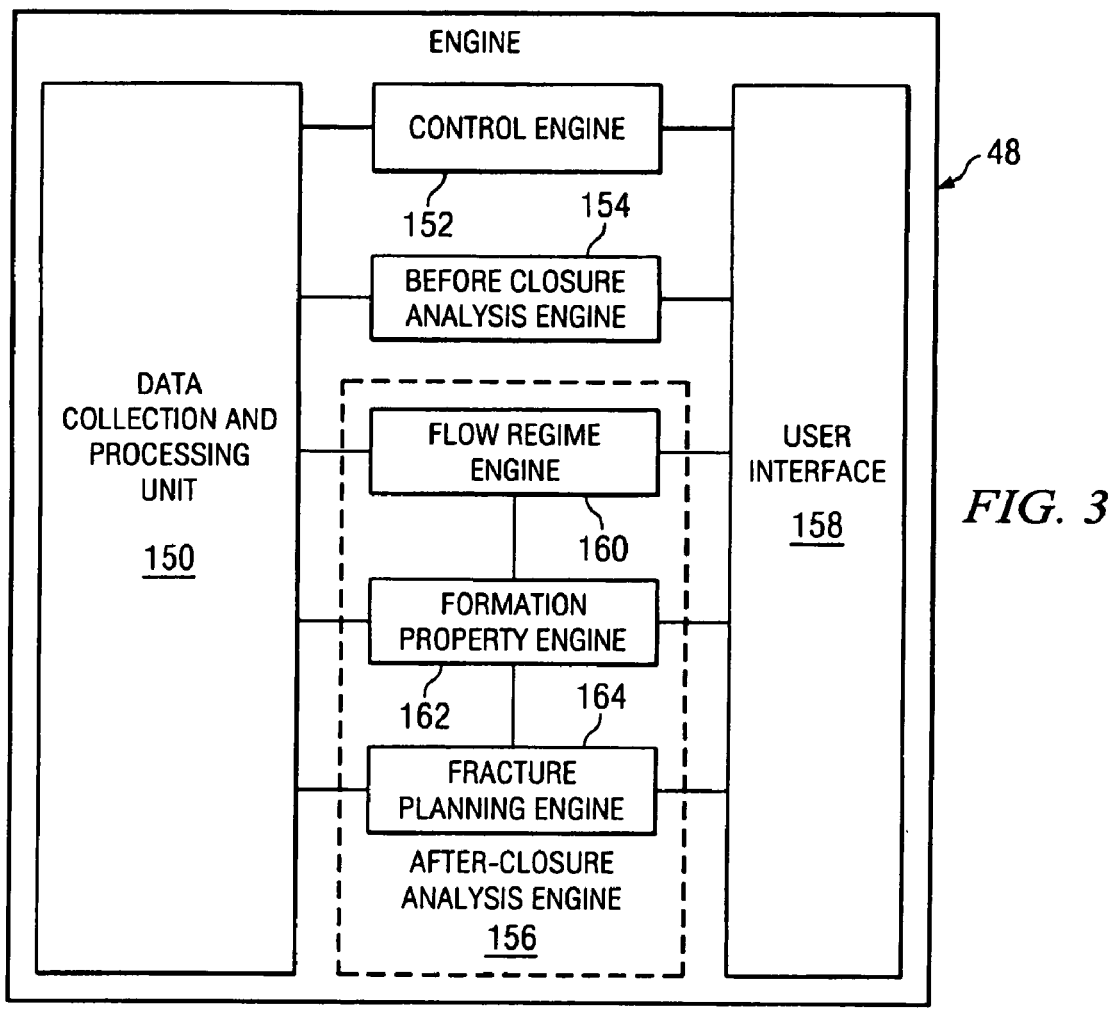
FIG. 3 illustrates one embodiment of the fracture control of FIG. 1.

FIG. 3 illustrates one embodiment of the fracture control system 46. In this embodiment, the fracture control system 46 is implemented as an integrated computer system such as a personal computer, laptop, or other stand-alone system. In other embodiments, the fracture control system 46 may be implemented as a distributed computer system with elements of the fracture control system 46 connected locally and/or remotely by a computer or other communication network.

The fracture control system 46 may comprise any processors or set of processors that execute instructions and manipulate data to perform the operations such as, for example, a central processing unit (CPU), a blade, an application specific integrated circuit (ASIC), or a field-programmable gate array (FPGA). Processing may be controlled by logic which may comprise software and/or hardware instructions. The software may comprise a computer readable program coded and embedded on a computer readable medium for performing the methods, processes and operations of the respective engines.

Referring to FIG. 3, the fracture control system 46 includes a data collection and processing unit 150, a control engine 152, a before-closure analysis engine 154, an after-closure analysis engine 156 and user interface 158. The fracture control system 46 and/or components of the fracture control system 46 may comprise additional, different, or other suitable components.

Data collection and processing unit 150 receives and/or communicates signals to and from surface and down-hole sensors 48 and 50 as well as pump controls 52. The collection and processing unit 150 may correlate received signals to a corresponding measured value, filter the data, fill in missing data and/or calculate data derivatives used by one or more of the control engine 152, before-closure analysis engine 154 and/or after-closure analysis engine 156. The data collection processing unit 150 may comprise data input/output (I/O) and a database or other persistent or non-persistent storage.

The control engine 152, before-closure analysis engine 154 and after-closure analysis engine 156 may each be coupled to the data collection and processing unit 150 and the user interface 158. Accordingly, each may access data collected and/or calculated and each may be accessed by an operator or other user via the user interface 158. The user interface 158 may comprise a graphical interface, a text based interface or other suitable interface.

The control engine 152 controls the fracture operation 10. In one embodiment, for example, the control engine 152 may control the pump trucks 40 and fluid valves to stop and start the fracture operation 10 as well as to start and stop the pad phase, proppant phase and/or flush phase of the fracture operation 10.

The before-closure analysis engine 154 analyzes before-closure data to determine formation properties of the reservoir 14 and of the well 12. In a particular embodiment, the before-closure analysis engine 154 may provide G-function analysis and transient analysis. In this embodiment, the G-function analysis may identify the leak-off mechanism and provide a definitive indication of the fracture closure stress. The leak-off mechanism may, comprise for example, normal, pressure dependent leak-off from open fissures, fracture height recession, fracture tip extension, and changing compliance. The transient analysis may be used to determine formation permeability. In one embodiment, transient analysis assumes the fracture propagation model and assumes the fracture has the same area during pumping and closure. The before-closure engine 154 may also determine the fracture 60 closure point. The closure point may be determined by using the G-function analysis.

The after-closure analysis engine 156 analyzes after-closure data to determine formation and residual fracture properties. In one embodiment, the after-closure analysis engine 156 comprises a flow regime engine 160, a formation property engine 162 and a fracture planning engine 160.

The flow regime engine 160 determines a flow regime of the fracture 60. In one embodiment, the flow regime engine 160 uses a graphical method to determine the flow regime based on data measured and collected during the fracture treatment 10. The flow regime engine 160 may also or instead use computational or other suitable methods to determine the flow regime. In a particular embodiment, the after-closure analysis engine 160 may make no assumptions regarding the flow regime dominating the reservoir 14 after closure of the fracture 60 or how the fracture 60 propagates during the fracture treatment 10.

In the embodiment in which the flow regime engine 160 uses the graphical method to determine the flow regime, the flow regime engine 160 may plot the derivative of the pressure differential with respect to time $p_{fo}$ versus total time for the fracture treatment 10 on a log-log scale to generate a derivative graph. The derivative graph is indicative of the flow regime of the fracture 60. In a particular embodiment, the derivative graph may plot $\log((t_p + \Delta t) \partial p_{fo}/\partial t)$ versus $\log(t_p + \Delta t)$, where $p_{fo}$ is pressure during fall-off period (psia), t is total time (hrs.), $t_p$ is injection time (hrs.) and $\Delta t$ is shut in time (hrs.). The plot of the derivative graph will eventually follow a straight line, the slope of which indicates the flow regime.

The flow regime engine 160 may determine the slope of the straight line and use the slope to determine flow regime. For example, the flow regime engine 160 may determine that the pseudo-radial flow regime 100 dominates the fluid flow behavior after closure of the fracture 60 following the fracture treatment 10 if the slope of the straight line is −1, i.e., forms a horizontal line. In another example, the flow regime engine 160 may determine that the bilinear flow regime 110 dominates fluid flow behavior after closure of the fracture 60 following the fracture treatment 10 if the slope of the straight line is −0.75. In still another example, the flow regime engine 160 may determine that the linear flow regime 120 dominates the fluid flow behavior after closure of the fracture 60 following the fracture treatment 10 if the slope of the straight line comprises −0.5.

The flow regime engine 160 may output the determined flow regime to the data collection and processing unit 150 for storage, to the formation property engine 162 for use in determining formation properties and/or to the user interface 158 for review and/or use by the user.

The formation property engine 162 may determine formation properties of the reservoir 14 based on the determined flow regime and the data collected from the fracture treatment 10. In one embodiment, the reservoir property engine 162 may determine the formation properties of reservoir pressure and formation permeability. In this embodiment, as described in more detail below, the formation property engine 162 may use one or more of the following equations or graphs generated from the equations to determine the formation properties for the indicated flow regimes:

For the pseudo-radial flow regime 100:

$$p_{fo} - p_i = \frac{1694.4 \, V\mu}{kh} \frac{1}{(t_p + \Delta t)} \quad \text{(pseudo-radial 1)}$$

$$\log(p_{fo} - p_i) = \log\left(\frac{1694.4 \, V\mu}{kh}\right) - \log(t_p + \Delta t) \quad \text{(pseudo-radial 2)}$$

$$\log\left(t \frac{\partial p_{fo}}{\partial t}\right) = \log\left[\frac{1694.4 \, V\mu}{kh}\right] - \log(t_p + \Delta t) \quad \text{(pseudo-radial 3)}$$

$$\log\left(t^2 \frac{\partial p_{fo}}{\partial t}\right) = \log\left[\frac{1694.4 \, V\mu}{kh}\right] \quad \text{(pseudo-radial 4)}$$

For the bilinear flow regime 110:

$$p_{fo} - p_i = 264.6\frac{V}{h}(\mu)^{0.75}\left(\frac{1}{\phi c_t k}\right)^{0.25}\frac{1}{\sqrt{k_f w_f}}\left(\frac{1}{t_p + \Delta t}\right)^{0.75} \quad \text{(bilinear 1)}$$

$$\log(p_{fo} - p_i) = \quad \text{(bilinear 2)}$$
$$\log\left(264.6\frac{V}{h}(\mu)^{0.75}\left(\frac{1}{\phi c_t k}\right)^{0.25}\frac{1}{\sqrt{k_f w_f}}\right) - 0.75\,\log(t_p + \Delta t)$$

$$\log\left(t\frac{\partial p_{fo}}{\partial t}\right) = \quad \text{(bilinear 3)}$$
$$\log\left(198.45\frac{V}{h}(\mu)^{0.75}\left(\frac{1}{\phi c_t k}\right)^{0.25}\frac{1}{\sqrt{k_f w_f}}\right) - 0.75\,\log(t_p + \Delta t)$$

$$\log\left(t^2\frac{\partial p_{fo}}{\partial t}\right) = \quad \text{(bilinear 4)}$$
$$\log\left(198.45\frac{V}{h}(\mu)^{0.75}\left(\frac{1}{\phi c_t k}\right)^{0.25}\frac{1}{\sqrt{k_f w_f}}\right) + 0.25\,\log(t_p + \Delta t)$$

For the linear flow regime 120:

$$p_{fo} - p_i = 31.05\frac{V}{4h}\left(\frac{\mu}{\varphi c_t k L_f^2}\right)^{0.5}\left(\frac{1}{t_p + \Delta t}\right)^{0.5} \quad \text{(linear 1)}$$

$$\log(p_{fo} - p_i) = \log\left[31.05\frac{V}{4h}\left(\frac{\mu}{\varphi c_t k L_f^2}\right)^{0.5}\right] - 0.5\,\log(t_p + \Delta t) \quad \text{(linear 2)}$$

$$\log\left(t\frac{\partial p_{fo}}{\partial t}\right) = \log\left[15.525\frac{V}{4h}\left(\frac{\mu}{\varphi c_t k L_f^2}\right)^{0.5}\right] - 0.5\,\log(t_p + \Delta t) \quad \text{(linear 3)}$$

$$\log\left(t^2\frac{\partial p_{fo}}{\partial t}\right) = \log\left[15.525\frac{V}{4h}\left(\frac{\mu}{\varphi c_t k L_f^2}\right)^{0.5}\right] + 0.5\,\log(t_p + \Delta t) \quad \text{(linear 4)}$$

$$t = \frac{60.675\phi\mu c_t L_f^2}{k}hr \quad \text{(linear 5)}$$

$c_t$  total formation compressibility (psi)
$h$  net pay thickness (ft)
$k$  Formation permeability (md)
$k_f$  Fracture conductivity (md-ft)
$L_f$  Fracture half length (ft)
$p_{fo}$  Pressure during fall-off period (psia)
$p_i$  Initial reservoir pressure (psia)
$t$  Time (hrs)
$t_p$  Pumping time (hrs)
$V$  Injected volume into the chamber (bbl)
$\Delta t$  Shut-in time (hrs)
$w_f$  Fracture width
$\mu$  Viscosity (cp)
$\phi$  Porosity For each flow regime, equation 1 describes the behavior of the pressure data during the post-closure period of the fracture treatment 10. Equations 2-4 provide specialized log-log and derivative forms of equation 1. In particular equation 2 is a log of equation 1 while equations 3-4 are derivatives and logs of equation 1.

For the pseudo-radial flow regime 100, generating the derivative graph using equation pseudo-radial 2 yields a straight line with a slope of −1. Equation pseudo-radial 3 is independent of initial reservoir pressure, thus its plot is only a function of the observed pressure and time. Generating the derivative graph using equation pseudo-radial 3 also yields a straight line with a slope of −1. Equation pseudo-radial 4 is a variation on equation pseudo-radial 3 that may be used for the same purpose. However, equation pseudo-radial 4 produces a straight line with a slope of 0.

To determine formation properties for the pseudo-radial flow regime 100 the formation property engine 162 may plot pressure and time data using equation pseudo-radial 1 to generate a Cartesian graph of $p_{fo}-p_i$ versus $1/(t_p+\Delta t)$. The formation property engine 162 may determine the intercept from the Cartesian graph which is the reservoir pressure. With the reservoir pressure, formation permeability may be determined from equations pseudo-radial 1-4. In a particular embodiment, the formation property engine 162 determines formation permeability using equation to generate a logarithmic plot of $(p_{fo}-p_i)$ versus $(t_p+\Delta t)$. In a specific embodiment, the intercept of this plot, $b_r$, may be used to determine formation permeability for the pseudo-radial flow regime 100 using $$k = \left(\frac{1694.4V\mu}{b_r h}\right).$$

In this case, viscosity of the formation fluid is used.

For bilinear flow regime 110, generating the derivative graph using equation bilinear 2 yields a straight line with a slope of −0.75. Equation bilinear 3 is independent of initial reservoir pressure, thus the plot is the only function of the observed pressure and time. Generating the derivative graph using equation bilinear 3 also yields a straight line with a slope of −0.75. Equation bilinear 4 is a variation of bilinear equation 3 that may be used for the same purpose. However, equation bilinear 4 produces a straight line with a slope of 0.25.

To determine formation properties for the bilinear flow regime 110, the formation property engine 162 may plot pressure and time data using equation bilinear 1 to generate a Cartesian graph of $p_{fo}-p_i$ versus $(1/(t_p+\Delta t))^{0.75}$. The formation property engine 162 may determine the intercept from the Cartesian graph which is a reservoir pressure. With a reservoir pressure, formation permeability may be determined from equations bilinear 1-4. In a particular embodiment, the formation property engine 162 may determine formation permeability using equation bilinear 2 to generate a logarithmic plot of $(p_{fo}-p_i)$ versus $(t_p+\Delta t)$.

In a specific embodiment, for the bilinear flow regime 110, the intercept, $b_r$, is a function of both permeability and fracture conductivity and may be directly used to determine formation permeability using $$k = 264.6\frac{V}{h}\frac{\mu}{b_r}\frac{1}{(2.637 t_{ef})^{0.25}}$$

where $t_{ef}$ is the time to end of the bilinear flow. This calculation assumes that fracture length did not change and relies on observance of the end of the bilinear flow. If the end of the bilinear flow period is not observed for the fracture treatment 10, the last point on the straight line with slope of −0.75 may be used to calculate an upper bound of the formation permeability. For this calculation, viscosity of the filtrate fluid that leaked into the formation during the minifracture test may be used as the bilinear flow regime 110 reflects conditions inside and near the fracture 60.

For the linear flow regime 120, generating the derivative graph using equation linear 2 yields a straight line with a slope of −0.5. Equation linear 3 is independent of initial reservoir pressure, thus the plot is only a function of the observed pressure and time. Generating the derivative graph using equation linear 3 also yields a straight line with a slope of −0.5. Equation linear 4 is a variation of equation 3 and may be used for the same purpose. However, equation linear 4 produces a straight line with a slope of 0.5.

To determine formation properties for the linear flow regime 120, the formation property engine 162 may plot pressure and time data according to equation 1 to generate a Cartesian graph. The formation property engine 162 may determine the intercept from the Cartesian graph which is the reservoir pressure. With the reservoir pressure, formation permeability may be determined from equations 1-4. In a particular embodiment, the formation property engine 162 may determine formation permeability using equation 2. The end of linear flow (end of −0.5 for equation linear 3 and 0.5 for equation linear 4) occurs at dimensionless time of 0.016 and may be calculated using equation linear 5.

The formation property engine 162 may provide the reservoir pressure and/or formation permeability to the data collection and processing unit 150 for storage, to the fracture planning engine 162 for planning of a subsequent fracture treatment or to the user interface 158 for review and use by the user. The fracture planning engine 164 may modify pump times, pump pressures, fracture fluids including the pad, proppants and flush, based on the formation properties. The modification of the subsequent fracture treatment may include planning of the subsequent fracture treatment based on the formation properties or may comprise any adjustment to a planned fracture treatment to improve the viability, usefulness, usability, ease of use, efficiency, accuracy, cost or result of the subsequent fracture treatment.

Figure 4A:
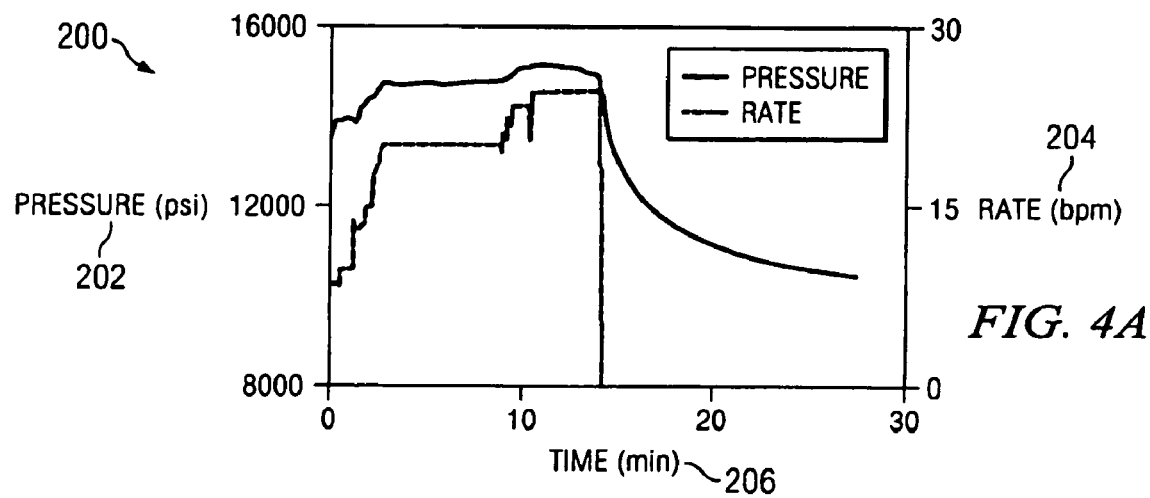
Figure 4B:
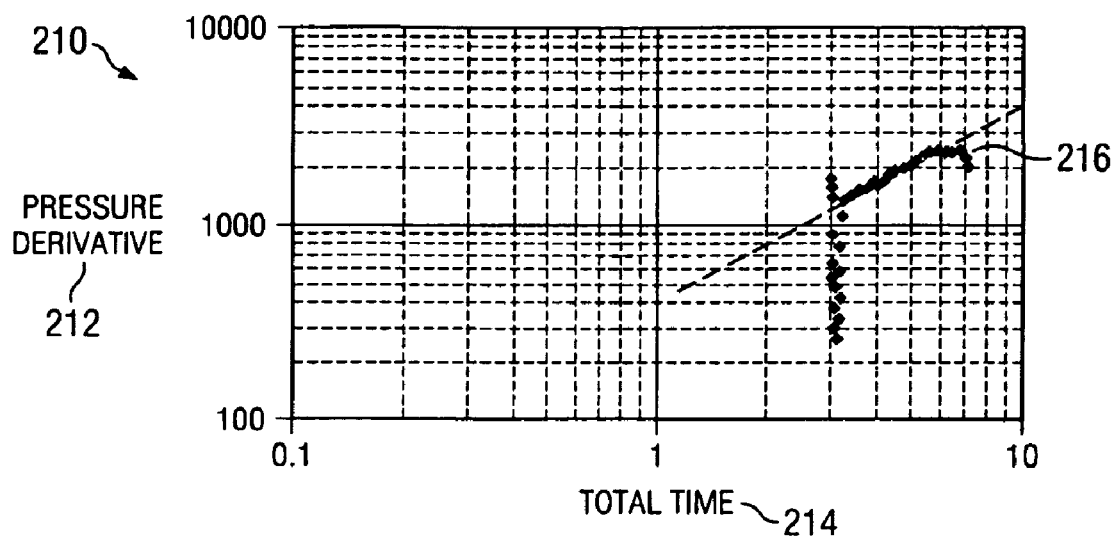
Figure 4C:
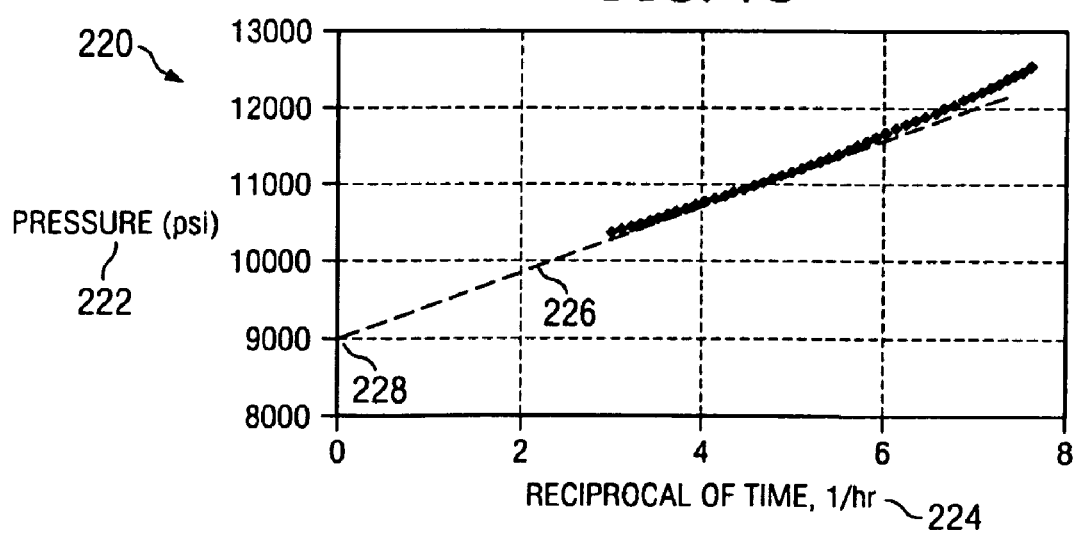

FIGS. 4A-D illustrate exemplary graphs for the pseudo-radial flow regime 100. In particular, FIG. 4A illustrates a treatment graph 200 for fracture treatment 10. FIG. 4B illustrates a derivative graph 210. FIG. 4C illustrates a Cartesian graph 220. FIG. 4D illustrates a log-log graph 230.

Referring to FIG. 4A, the treatment graph 200 plots bottom hole pressure 202 and injection rate 204 versus time 206 for the fracture treatment 10. Bottom hole pressure 202, injection rate 204 and time 206 may each be measured using one or more instruments or determined from or otherwise based on measured parameters. The fracture treatment 10 of FIG. 4A comprise an average injection rate of 18.8 bpm, with variations from 5 to 25 bpm. The instantaneous shut-in pressure (ISIP) was 13,760 psi, which resulted in a 0.97 psi/ft fracture gradient. The G-function analysis of the before-closure analysis engine 154 indicates closure at 12,578 psi.

Referring to FIG. 4B, the derivative graph 210 plots the derivative of pressure with respect to time 212 versus total time 214 on a log-log scale. From the derivative graph 210, the flow regime engine 160 determines the plot 216 follows a straight line having a slope of −1. From the slope, the flow regime engine 160 determines the after-closure period of the fracture treatment 10 is dominated by the pseudo-radial flow regime 100.

Referring to FIG. 4C, the Cartesian graph 220 plots bottom-hole pressure 222 versus the time reciprocal 224 to determine the intercept 228 of a straight line 226 at reciprocal time 0 (infinite shut-in time) which is the reservoir pressure. For exemplary plot 220, reservoir pressure is 9,000 psi.

Referring to FIG. 4D, the log-log graph 230 plots the change in pressure 232 versus the time reciprocal 234 using the reservoir pressure. The intercept of the straight line 238 is determined. In the exemplary embodiment, the intercept is 420 psi which may used to calculate a permeability of 7.12 md where net pay thickness is 20 ft, viscosity is 0.0037 cp and injected volume is 288.6 bbl. In one embodiment, height may be determined from logs, viscosity is a fluid property, and injected volume is known as a test parameter.

Figure 5B:
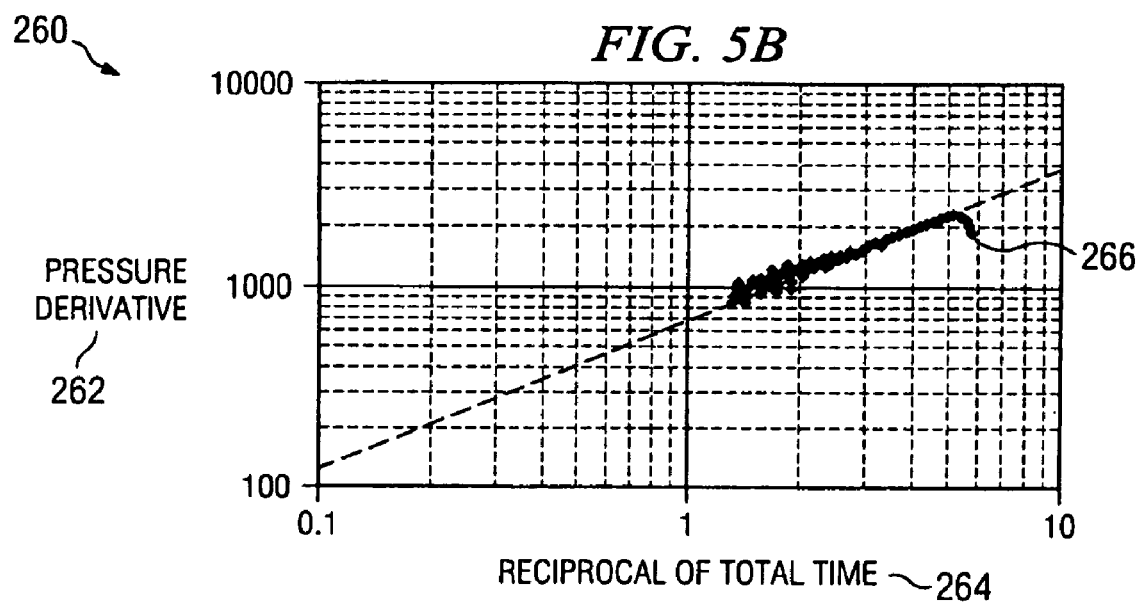
Figure 5C:
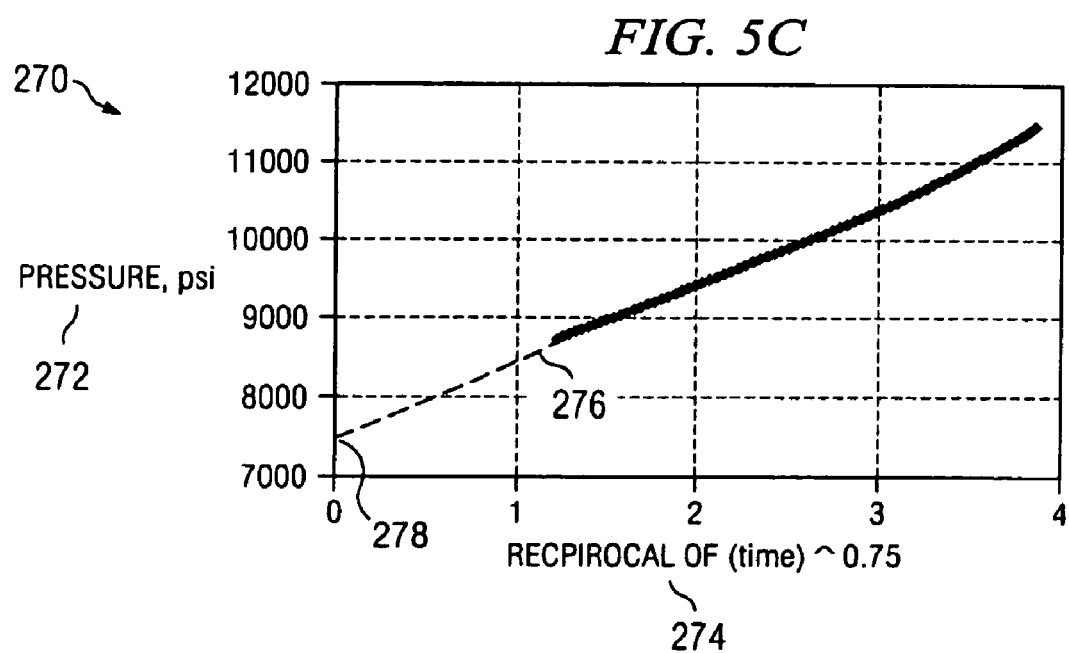
Figure 5D:
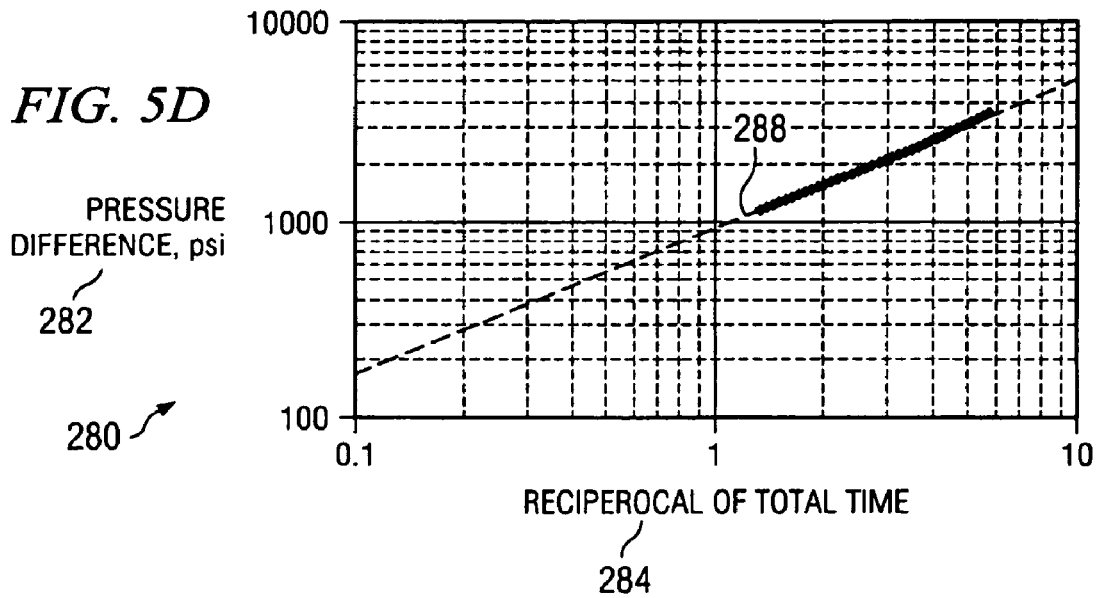

FIGS. 5A-D illustrate exemplary graphs for the bilinear flow regime 110. In particular, FIG. 5A illustrates a treatment graph 250 for another fracture treatment 10. FIG. 5B illustrates a derivative graph 260. FIG. 5C illustrates a Cartesian graph 270. FIG. 5D illustrates log-log graph 280.

Referring to FIG. 5A, the treatment graph 250 plots bottom-hole pressure 252 and injection rate 254 versus time 256 for the fracture treatment 10. Bottom-hole pressure 252, injection rate 254 and time 256 may each be measured using one or more instruments or determined or otherwise based on measured parameters. The fracture treatment 10 of FIG. 5A comprises a constant injection rate of 10.5 bpm. The instantaneous ISIP was 13,508 psi, which resulted in a 1.14 psi/ft fracture gradient. The G function analysis of the before-closure analysis engine 154 indicates closure at 11,505 psi.

Referring to FIG. 5B, the derivative graph 260 plots the derivative of pressure with respect to time 262 versus total time 264 on a log-log scale. From the derivative graph 260, the flow regime engine 160 determines the plot 266 follows a straight line having a slope of 0.75. From the slope, the flow regime engine 160 determines the after-closure period of the fracture treatment 10 is dominated by the bilinear flow regime 110.

Referring to FIG. 5C, the Cartesian graph 270 plots bottom-hole pressure 272 versus the time reciprocal 274 to determine the intercept 278 of the straight line 276 at reciprocal time 0 which is a reservoir pressure. For exemplary plot 276, reservoir pressure is 7,550 psi.

Referring to FIG. 5D, the log-log graph 280 plots a change in pressure 282 versus the time reciprocal 284 using the reservoir pressure. The intercept of the straight line 288 is determined. In the exemplary embodiment, the intercept is 933 psi which may be used with the final point on the straight line to calculate an upper bound of permeability of 0.5763 md where net pay thickness is 27 ft., viscosity is 0.344 cp and injected volume is 189.7 bbl.

As previously described, the linear flow regime 120 may be similarly determined. As also previously described, pseudo-radial, bilinear and linear flow may be determined for horizontal and other wells. For example, for a vertical fracture intersecting a horizontal well, the flow regime may be determined as described in detail above if the fracture is longitudinal relative to the horizontal well. If the fracture is transverse with respect to the horizontal well bore, then we may have, for example the pseudo-radial flow regime 100 if the fracture closes with little or no fracture length or the shut-in time is very long; a linear-radial flow regime corresponding to the bilinear flow regime 110 in a vertical well case or the linear flow regime 120 if the dimensionless fracture conductivity is very high, for example. For the linear-radial flow regime which is described by Soliman, M. Y., Hunt, J. L., and El-Rabaa, A.: "Fracturing Aspects of Horizontal Wells," JPT, August 1990, the basic equations may be used to develop specialized plots for determining fracture and formation properties. The above-referenced article is reproduced below.

Figure 6:
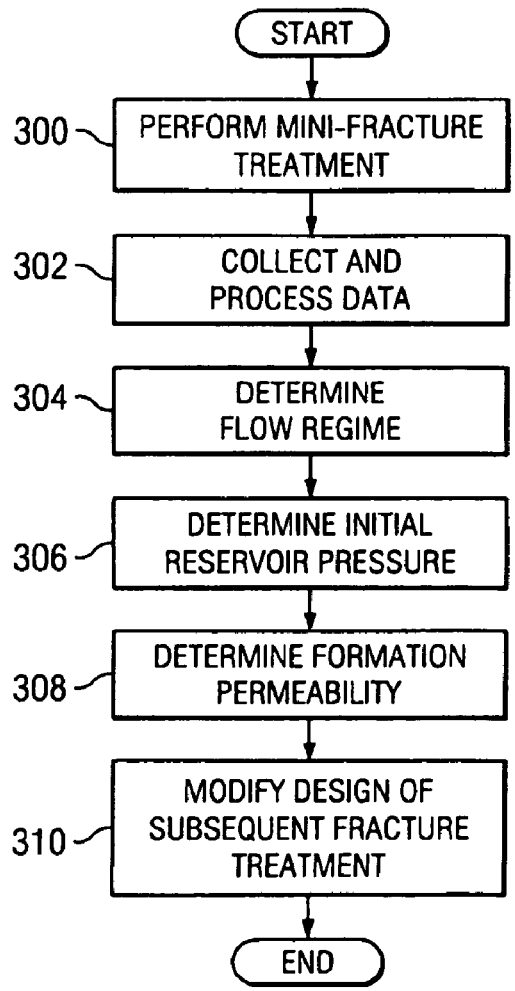
FIG. 6 illustrates a method for determining fracture and formation properties based on a fracture treatment.

FIG. 6 illustrates one embodiment of a method for determining formation properties based on a fracture treatment 10. In this embodiment, formation properties are determined based on a mini fracture test treatment. The method begins at step 300 in which the mini fracture test treatment is performed. As previously described, the mini fracture test treatment may comprise a pad phase, a proppant phase and a flush phase. Next, at step 302, data is collected from the mini fracture treatment. The data may comprise pressure, rate and time data as well as other data used in the flow regime equations. For example, the data may include reservoir data such as fluid viscosity, net pay thickness and total formation height as well as well data such as well bore radius. The data may be processed by filtering the data, filling in missing data, determining differentials and derivatives and/or storing the data.

At step 304, the flow regime is determined. As previously described, the flow regime may be a pseudo-radial flow regime 100, a bilinear flow regime 110, a linear flow regime 120 or other suitable flow regime. The flow regime may be determined based on a function of pressure versus time for the mini fracture test treatment. As previously described, in one embodiment, the flow regime may be determined based on the derivative graph plotting the log of pressure with respect to time versus the log of total time.

The initial reservoir pressure may be determined at step 306. The initial reservoir pressure is determined based on the flow regime using equations, methods, processes and/or data specific to the flow regime. As previously described, the initial reservoir pressure may be determined from the intercept of the Cartesian graph for the flow regime.

At step 308, formation permeability is determined. The formation permeability may be determined based on the reservoir pressure and the flow regime determined. In one embodiment, as previously described, the formation permeability is determined using the intercept of the log-log graph.

As previously described, these and/or other reservoir properties may instead be determined computationally using the indicated equations, derivatives thereof or other suitable equations.

At step 310, a subsequent fracture is modified based on the reservoir properties determined from the mini fracture test treatment. As previously described, the pump times, pump pressure and/or fracture fluids of the subsequent fracture treatment may be modified based on the reservoir properties. Step 310 leads to the end of the process.

The above-referenced article, "Fracturing Aspects of Horizontal Wells," is reproduced below.

Summary. This paper discusses the main reservoir engineering and fracture mechanics aspects of fracturing horizontal wells. Specifically, the paper discusses fracture orientation with respect to a horizontal wellbore, locating a horizontal well to optimize fracture height, determining the optimum number of fractures intercepting a horizontal well. and the mechanism of fluid flow into a fractured horizontal well.

Introduction. Interest in horizontal well drilling and completions has increased during the last few years. The significant advances in drilling and monitoring technology have made it possible to drill, guide, and monitor horizontal holes, making horizontal drilling not only possible but also consistently successful. Most wells have been completed as drainholes. These drainholes have been used in primary production and in EOR.

Papers on drilling, completion, well testing, and increased production of horizontal vs. vertical wells have been presented in the petroleum literature.[1-10] Many papers[2-5] have dealt with steady-state production increase of horizontal wells over vertical wells. Graphs and equations have been presented for calculating steady-state ratios for both fractured and unfractured wells. Ref. 2 provides a recent review of this technology. Other authors[6-9] have studied the transient behavior of pressure response during a drawdown or a buildup of a drainhole. The literature lacks comprehensive studies on fracturing horizontal wells, and none of the studies cited above discussed this subject. Only Karcher et al.[10] studied production increase caused by multiple fractures intercepting a horizontal hole. Using a numerical simulator, Karcher studied steady-state behavior of infinite-conductivity fractures.

Stability of horizontal holes during drilling is another important aspect of horizontal well technology. It has been found[11] that the degree of stability of horizontal holes depends on the relative magnitude of the three principal stresses and the orientation of the wellbore with respect to the minimum horizontal stress.

Although productivity of horizontal wells could be two to five times higher than productivity of vertical wells, fracturing a horizontal well may further enhance its productivity, especially when formation permeability is low. Presence of shale streaks or low vertical permeability that impedes fluid flow in the vertical direction could make fracturing a horizontal well a necessity.

This paper discusses fracturing horizontal wells from both reservoir engineering and fracture mechanics points of view. Our goal is to shed some light on important aspects of fracturing horizontal wells.

Stress magnitude and Orientation. The first parameter to be determined is the fracture orientation with respect to the wellbore. Because fractures are always perpendicular to the least principal stress, the questions actually concern wellbore- and stress-orientation measurements.

In what direction will induced fractures occur?
What is the anticipated fracture geometry?
What is the optimum length of the perforation interval?
What is the optimum treatment size?
What are the expected fracturing pressures?

Data necessary for planning a fracturing treatment are the mechanical properties of the formation, the orientation and magnitude of the least principal stress, the variation in stresses above and below the target formation, and the leakoff characteristics of the formation.

It is commonly accepted that, at depths usually encountered in the oil field, the least principal stress is a horizontal stress. It also can be shown that the induced fracture will be oriented perpendicular to the least principal stress. The result is that a fracture created by a treatment will be in a vertical plane. If the horizontal segment is drilled in the direction of the least stress, several vertical fractures may be spaced along its axis wherever perforations are present. This spacing is one of the design parameters to be selected. Usually, this is investigated with numerical simulators. If the horizontal segment is drilled perpendicular to the least stress, one vertical fracture will be created parallel to the well. FIGS. 1 and 2 show fracture direction vs. well direction.

When the wellbore is not in one of these two major directions, several scenarios may occur, depending on the angle between the wellbore and the stress direction and one the perforation distribution and density. In this paper, only the presence of fractures perpendicular or parallel to the wellbore is discussed.

Determining Magnitude and Orientation of Least Principal Stress. If field history does not clearly reveal the orientation and magnitude of the least principal stress, on-site tests should be performed to determine these parameters. Three methods to determine stress magnitude and/or orientation exist. Microfracturing, described by Daneshy et al.,[12] may be used to measure the least principal stress and fracture orientation directly. Long-spaced sonic logging may be used to estimate stress magnitude; however, logging has the disadvantage of ignoring tectonic stresses. Strain relaxation may also be used to estimate magnitude and orientation.[13] Because the openhole microfracturing technique is a direct measurement of stress magnitude and orientation, it is recommended for new reservoirs.

To collect the necessary data, it is recommended that, first, the well be drilled vertically through the pay zone and that tests to measure stress magnitude and orientation be performed. Drillstem tests and/or logging can be performed on the vertical section to determine other formation parameters.

At the end of these tests, the hole may be plugged back and kickoff can be performed in the direction determined by the microfracture test. In this manner, the most accurate determinations are made in the actual target formation, as close as practically possible to the location in which fracturing treatments will be performed, without drilling a new vertical well. FIG. 3 shows this procedure.

Fracture Direction With Respect to Wellbore. As mentioned earlier, deciding on fracture orientation with respect to the wellbore is extremely important. One should decide whether designs similar to those of FIGS. 1 and 2 should be considered.

If feasible, it is preferable to create effective multiple fractures because of the accelerated production they generate. Here, a simplified analytical model is used to study the effectiveness of fractures perpendicular to the wellbore. The model considered assumes a wellbore intercepting the fracture plane, as shown in FIG. 4. It assumes that fluid flows linearly from the formation into the fracture, and then flows radially inside the fracture into the wellbore. Although this assumption implies an early-time solution, the results are valid qualitatively over a longer time span. In this aspect, the model is similar to those of Cinco-Ley and Samaniego-V.[14] and Schulte.[15] To examine the effect of a tail-in technique on well performance, the model incorporated a step change in conductivity, similar to the method presented in Ref 16.

In our model, the fracture is assumed to have two distinct conductivities that are radially discontinuous. The governing partial differential equation and the final solution for both constant-rate and constant-pressure cases are presented in Appendices A and B. The governing equations were solved with the Laplace transform. The Laplace transformation of the solution was reinverted with the Stehfest algorithm.[17] Various aspects of the solution were studied and are presented in FIGS. 5 through 11.

FIG. 5 compares the performance of a vertical well that intercepts a vertical fracture with the performance of a horizontal well that intercepts a vertical fracture (perpendicular to well). As shown, for $C_{fD}=10$, the horizontal well has a significantly higher pressure drop for the same production rate. The high pressure drop encountered in the case of a horizontal well intercepting a vertical fracture results from the radial flow of fluid inside the fracture as fluid converges toward the wellbore. $C_{fD} \geq 50$ would produce a pressure drop similar to that of a vertical well that intercepts a vertical fracture with $C_{fD}=10$, which is evident if FIGS. 5 and 7 are compared.

Effect of Fracture Conductivity. In this section, the fracture orientation with respect to the wellbore is as shown in FIG. 4. The model is the same as considered previously.

As FIG. 5 shows, the high pressure drop exhibited by the horizontal well intercepting a vertical fracture perpendicular to the wellbore is caused by fluid within the fracture converging radially toward the wellbore. This is similar to the pressure drop around an unfractured well. If the wellbore radius increases, the pressure drop necessary to produce a well decreases (FIG. 6). FIG. 6 also implies that an infinite conductivity may exist inside the fracture up to the defined $r_{wD}$. For example, the curve for $r_{wD}=0.5$ can be explained as a curve for a very small radius fracture or that for a large-radius fracture with infinite conductivity up to a radius of $0.5x_f$ and $C_{fD}=10$ from a radius of $0.5x_f$ to a radius $x_f$.

Figure 7:
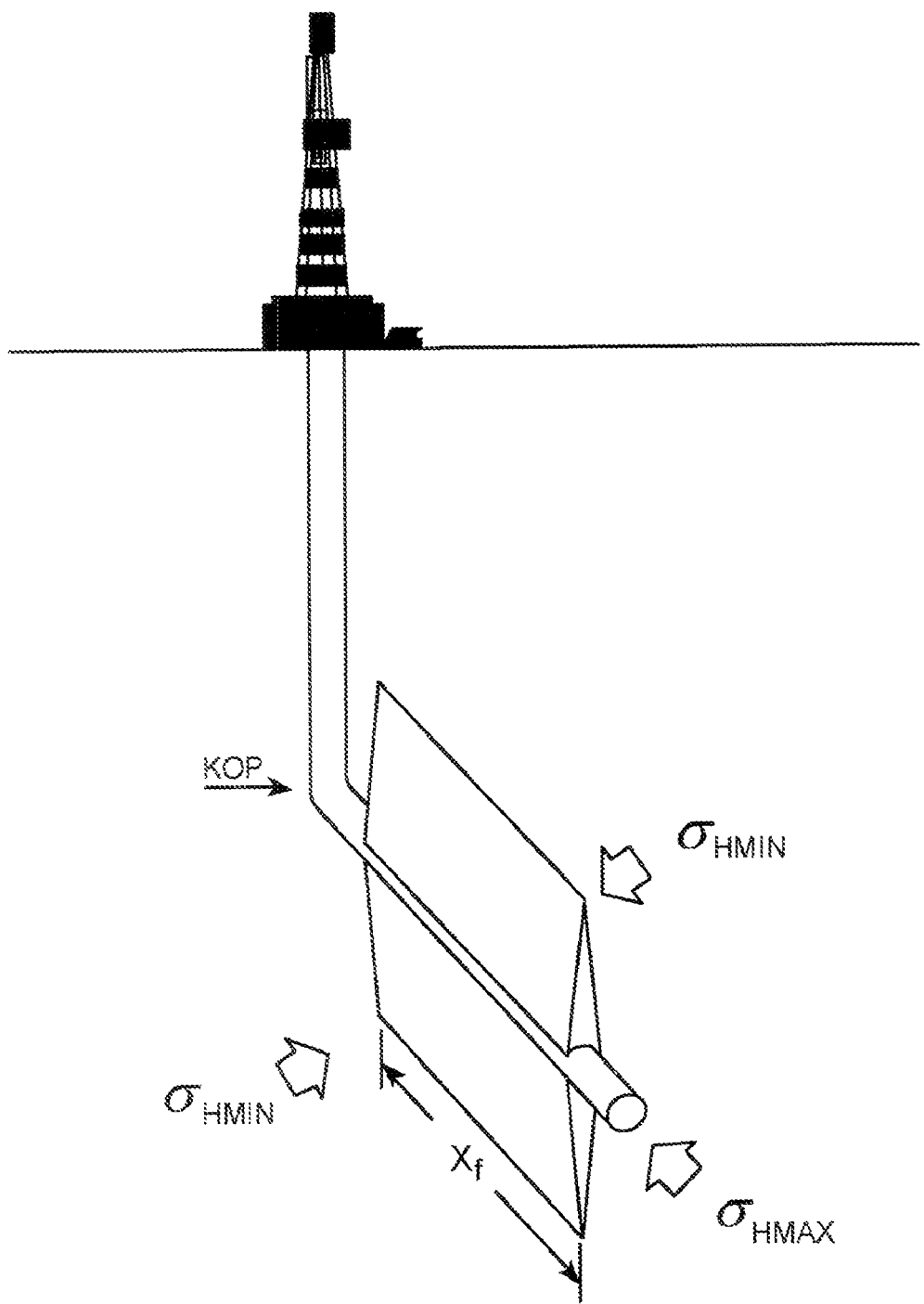
FIG. 7 illustrates a horizontal segment of a wellbore perpendicular to least stress ($\sigma_{Hmin}$)
Figure 8:
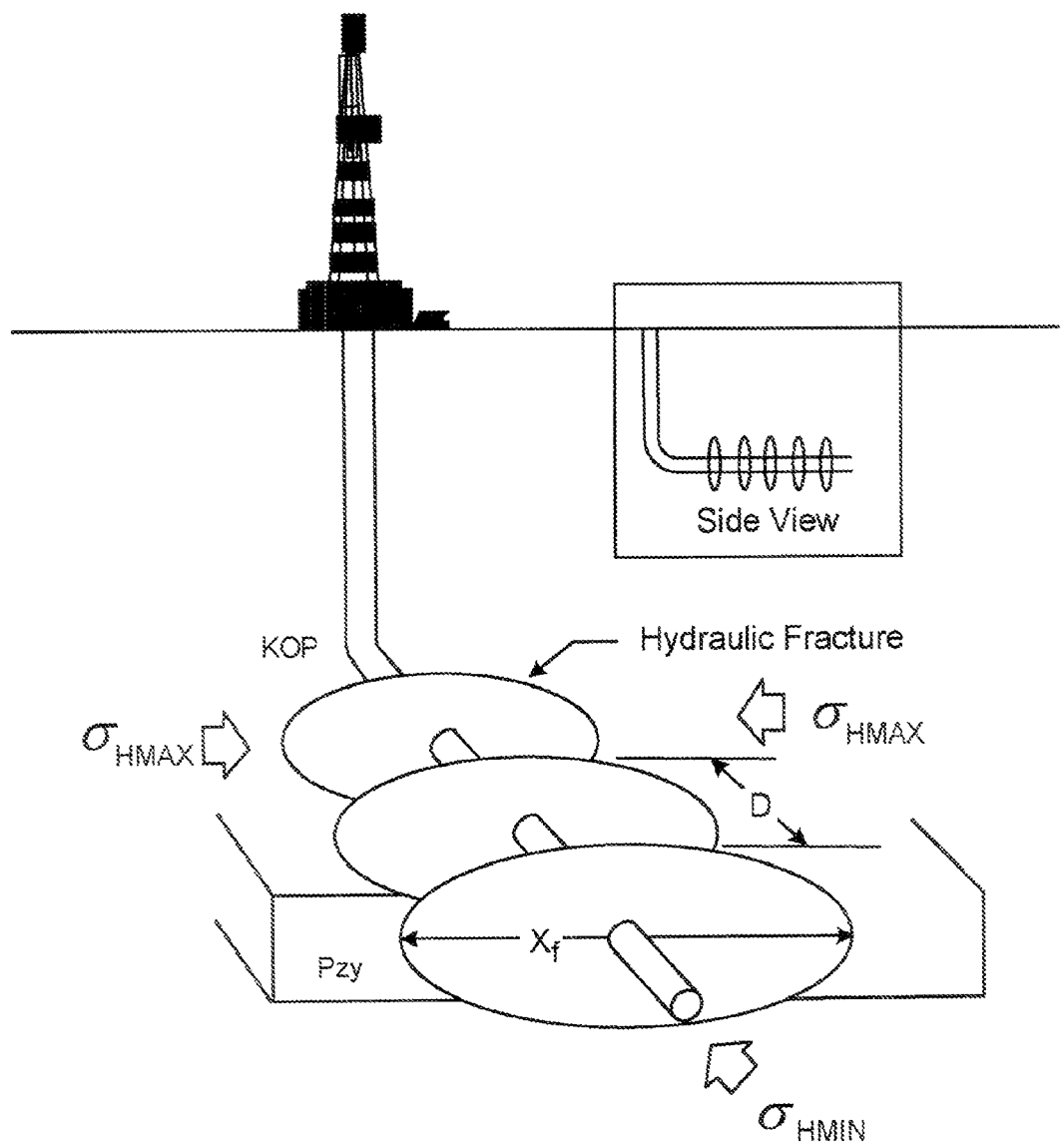
FIG. 8 illustrates a horizontal segment of a wellbore parallel to least stress ($\sigma_{Hmin}$)

The effect of higher-conductivity tail-in is examined further in FIGS. 7 and 8. FIG. 7 shows the effect of lower conductivity away from the wellbore. It is assumed that the first half of the fracture is maintained at $C_{fD}=500$ and that, for the second half, $C_{fD}$ was 50, 20, or 10. In the last three cases, fracture behavior was uniform with $C_{fD}$ 500 until $t_D=3\times10^{-7}$, where the curves exhibited a significant increase in pressure drop. FIG. 8 examines the effect of tail-in radius, where the radius of higher conductivity ($C_{fD}=50$) is set at 0.1, 0.3, and 0.5. FIG. 8 shows that deviation from the uniform fracture behavior depends on the tail-in radius.

Figure 9:
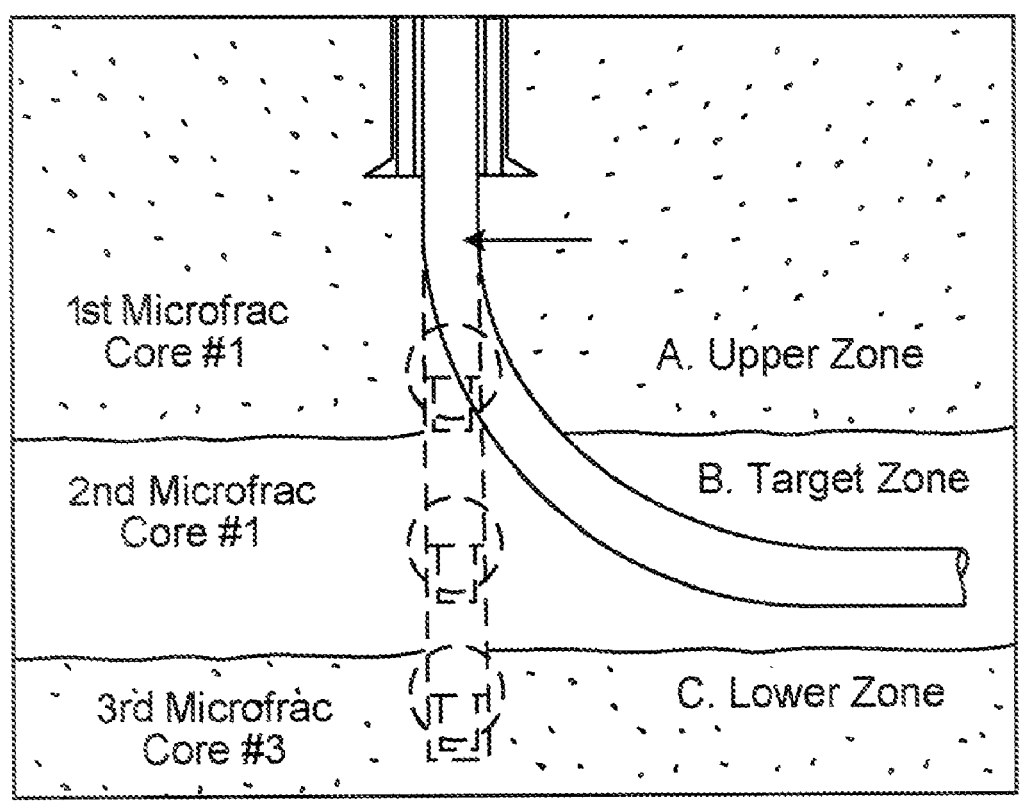
FIG. 9 illustrates vertical and horizontal segments of a wellbore.

FIGS. 5 through 8 show the importance of having high fracture conductivity, or at least high tail-in conductivity. FIG. 9, on the other hand, shows the devastating effect that lower conductivity near the wellbore can have. In FIG. 9, only 10% of the fracture dropped from $C_{fD}=50$ to $C_{fD}=10$, 5, or 1. FIG. 9 shows that, even at early time, well behavior was almost totally controlled by the lower-conductivity tail-in. At later times, the high conductivity will have a somewhat minor effect. FIG. 9 indicates that proppant damage near the wellbore should be avoided and that a tail-in with a strong proppant should be pumped into the fracture whenever feasible.

Figure 10:
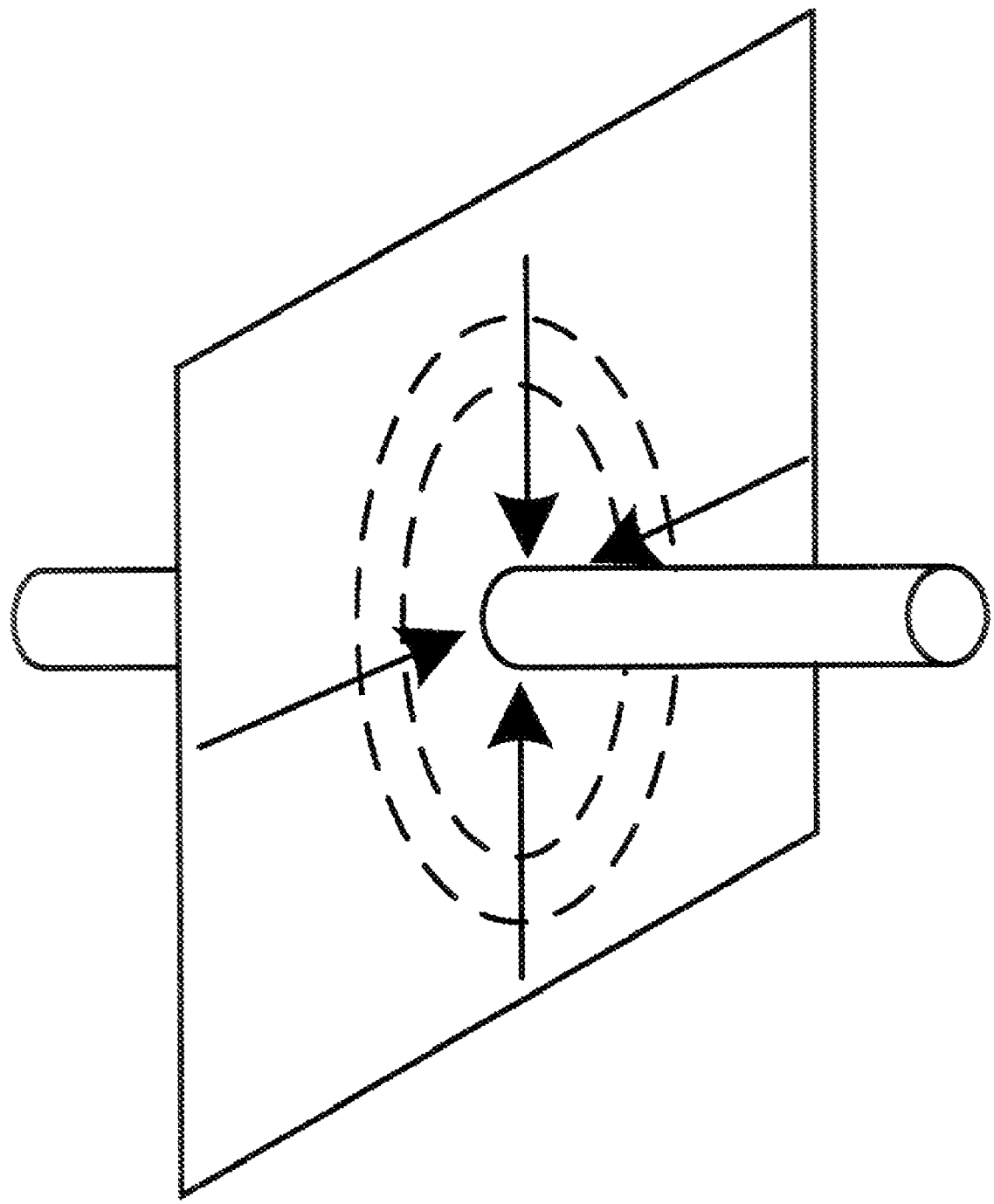
FIG. 10 illustrates a vertical fracture intercepting a horizontal well.
Figure 11:
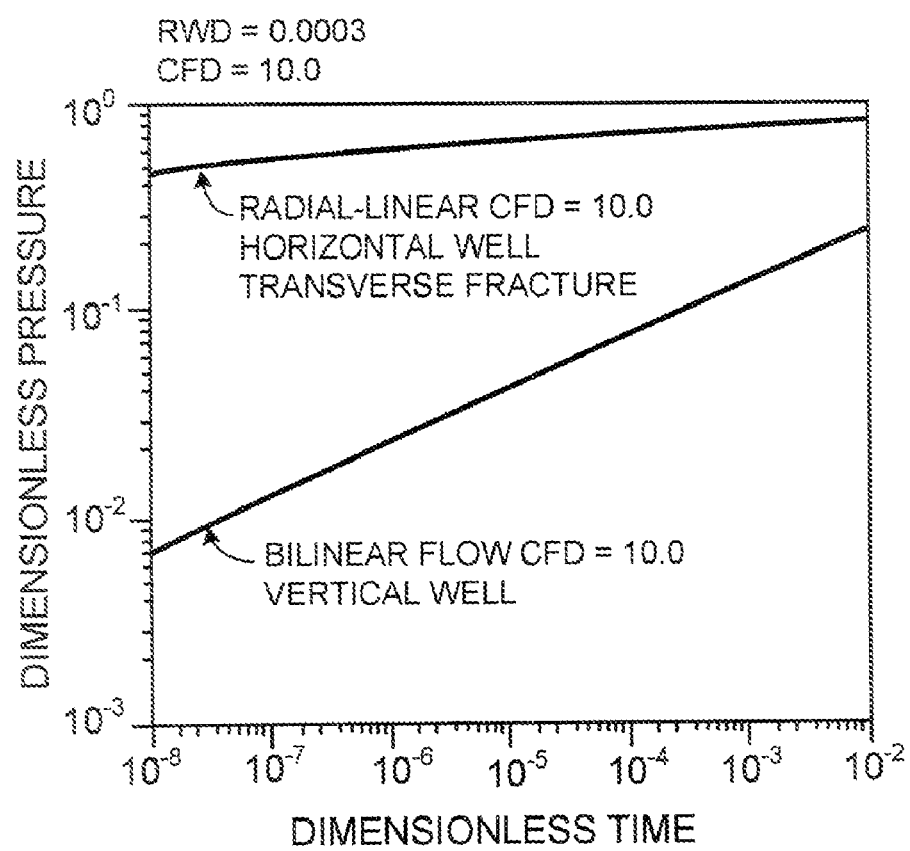
FIG. 11 is a graph showing a comparison of radial/linear flow to bilinear flow.

The parameters used to produce FIGS. 7 and 8 were also used to produce FIGS. 10 and 11. FIGS. 10 and 11, however, are based on constant flow pressure. Conclusions from FIGS. 7 and 8 are confirmed by FIGS. 10 and 11.

Previously work[18] showed that high fracture conductivity was necessary to minimize the cleanup effect following a fracturing treatment. In the case of a horizontal well intercepting a vertical fracture, cleanup becomes much more of a problem because of the radial convergence of fluid near the wellbore. The presence of higher water saturation near the wellbore effectively reduces fracture conductivity near the wellbore, resulting in behavior similar to low-conductivity tail-in. High fracture conductivity, therefore, is extremely important for horizontal wells.

This discussion agrees with conclusions reached by Soliman,[16,19] who stated that fracture performance depends on the magnitude and the distribution of conductivity and does not depend solely on the average of fracture conductivities, as concluded by Bennett et al.[20] Soliman showed that a conductivity distribution profile exists where a fracture with declining conductivity performs as well as a uniform fracture conductivity,[19] in spite of the difference in average fracture conductivity.

Determining the Optimum Number of Fractures. To determine the optimum number of fractures intercepting the horizontal wellbore that is necessary to produce the formation, the following assumptions were made.

1. Fractures are identical in physical dimensions (length, height, width, and conductivity).
2. Fractures are vertical and perpendicular to the wellbore axis.
3. Fracture conductivity is sufficiently high to be assumed infinite.
4. Because the horizontal section is assumed cemented, cased, and perforated at the sections where fractures are created, formation fluid cannot flow directly into the wellbore.

Figure 12:
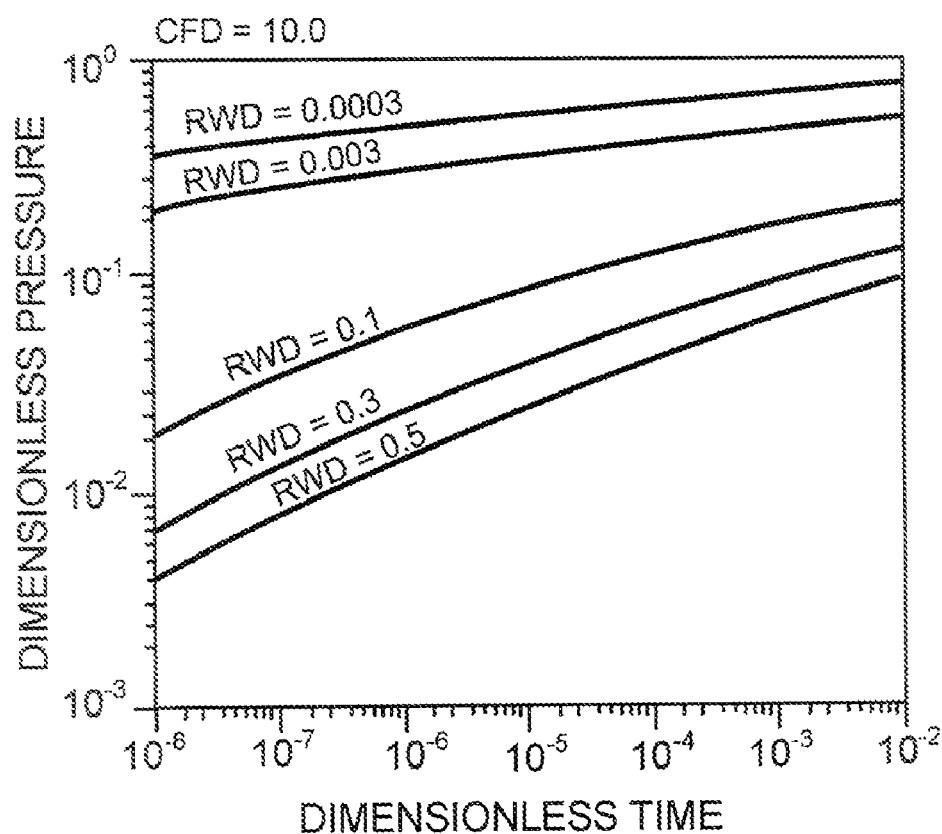
FIG. 12 is a graph showing an effect of increasing dimensionless wellbore radius.
Figure 13:
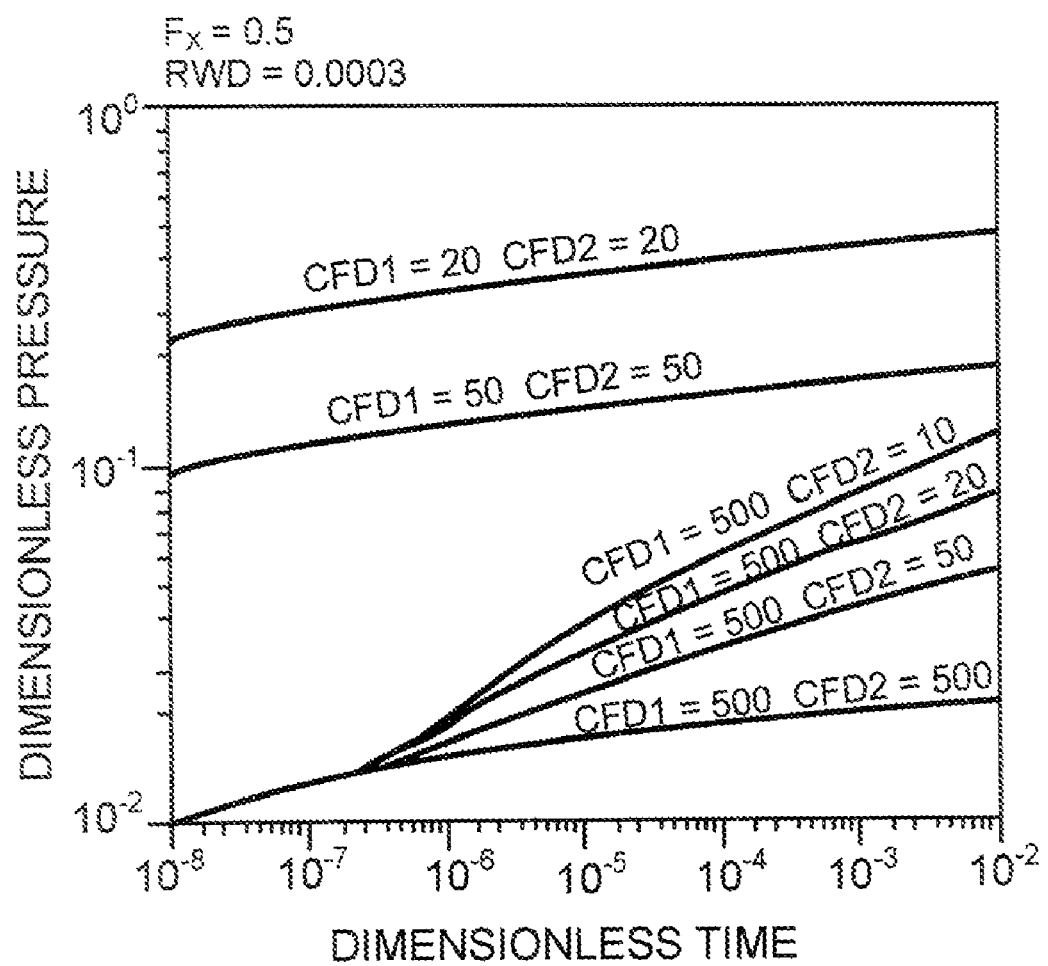
FIG. 13 is a graph showing an effect of tail-in with high conductivity.
Figure 14:
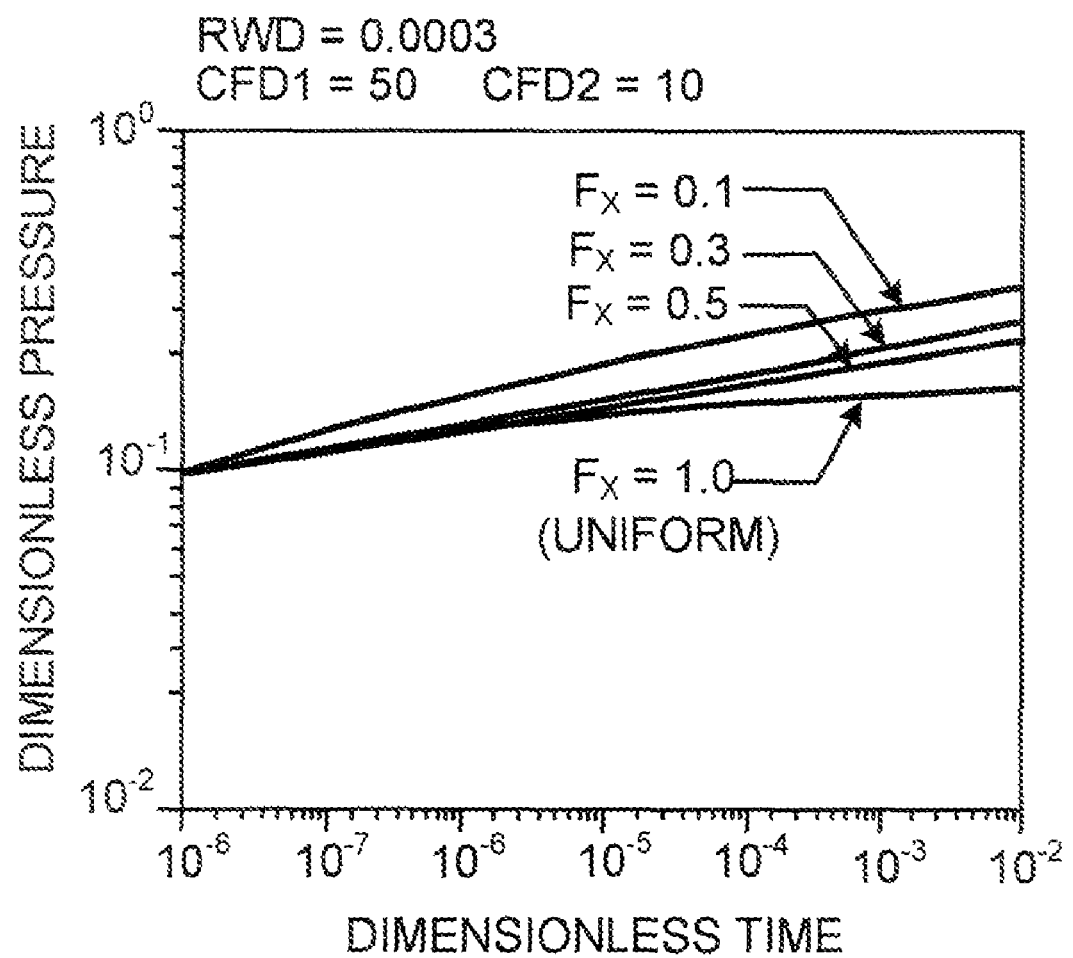
FIG. 14 is a graph showing an effect of increasing tail-in radius.
Figure 15:
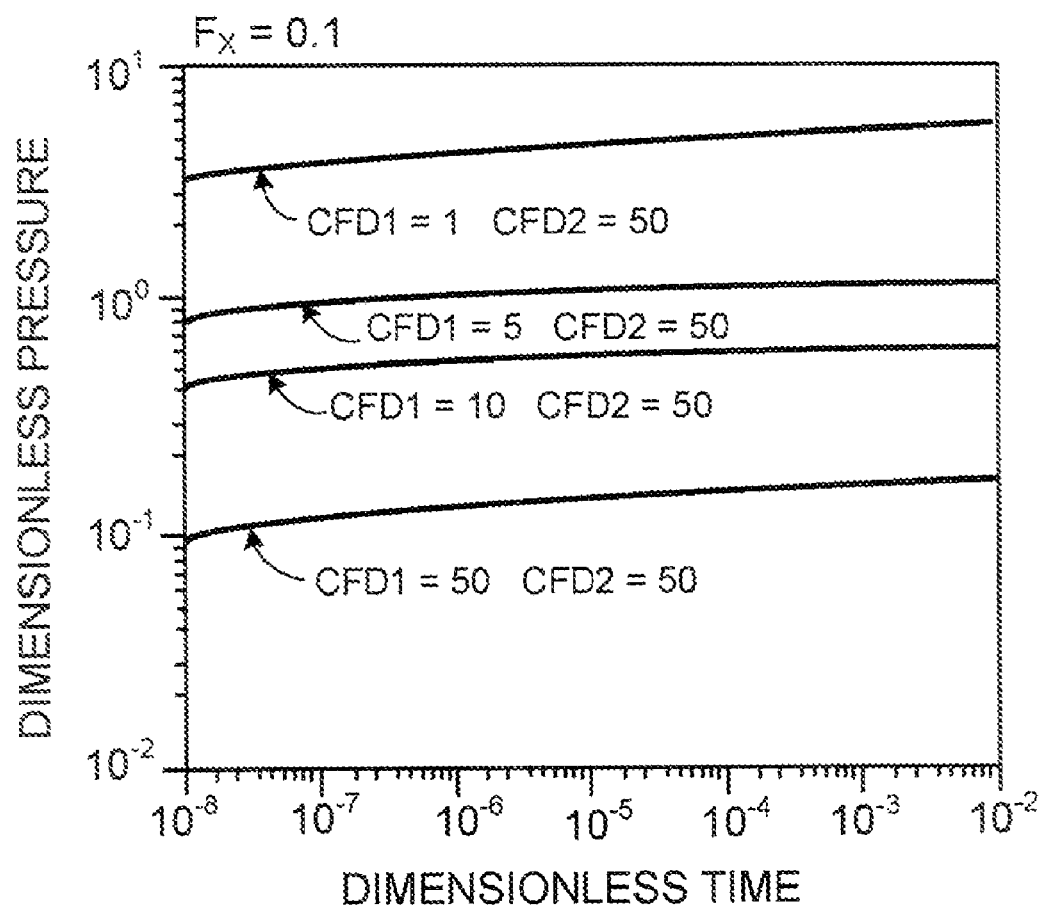
FIG. 15 is a graph showing an effect of decreasing conductivity near a wellbore.

The equations governing fluid flow in the formation and fracture can be solved with a single-phase finite-difference simulator. The simulator,[19-21] which solves the governing equations implicitly, was applied to an actual field case. Table 1 gives the reservoir properties, and FIG. 12 is a schematic representing one simulator run for the case of two fractures. FIGS. 13 through 15 show field case results.

TABLE 1

Well and Reservoir Parameters for FIGS. 19 through 22

| | |
|---|---|
| k, md | 0.10 |
| φ, % | 13 |
| h, ft | 272 |
| $p_i$, psia | 4,000 |
| $T_{bh}$, °F. | 150 |
| $p_{wf}$, psia | 50 |
| A, acres | 170 |
| $S_w$, % | 50 |
| $x_f$, ft | 136 |
| $c_f$, md-ft | 1,381 |
| w, in. | 0.19 |

In FIG. 13, total flow rate is plotted vs. the number of fractures at various times, while FIGS. 14 and 15 show cumulative production vs. time and number of fractures, respectively.

FIG. 13 shows that, initially, total flow rate increases as the number of fractures increases. The total flow rate reaches a maximum, and then it declines. The number of fractures at which the maximum flow rate occurs declines with time, reaching five fractures after 1 month but declining to only two fractures after 24 months. The decline in total flow rate is caused by reservoir depletion. The optimum number of fractures is better determined from FIGS. 14 and 15, which show that, for the case under consideration, five fractures represent the optimum number of fractures necessary to produce the reservoir. This number may vary if economic considerations are included. Note that the optimum number of fractures depends on formation and fluid properties.

Figure 16:
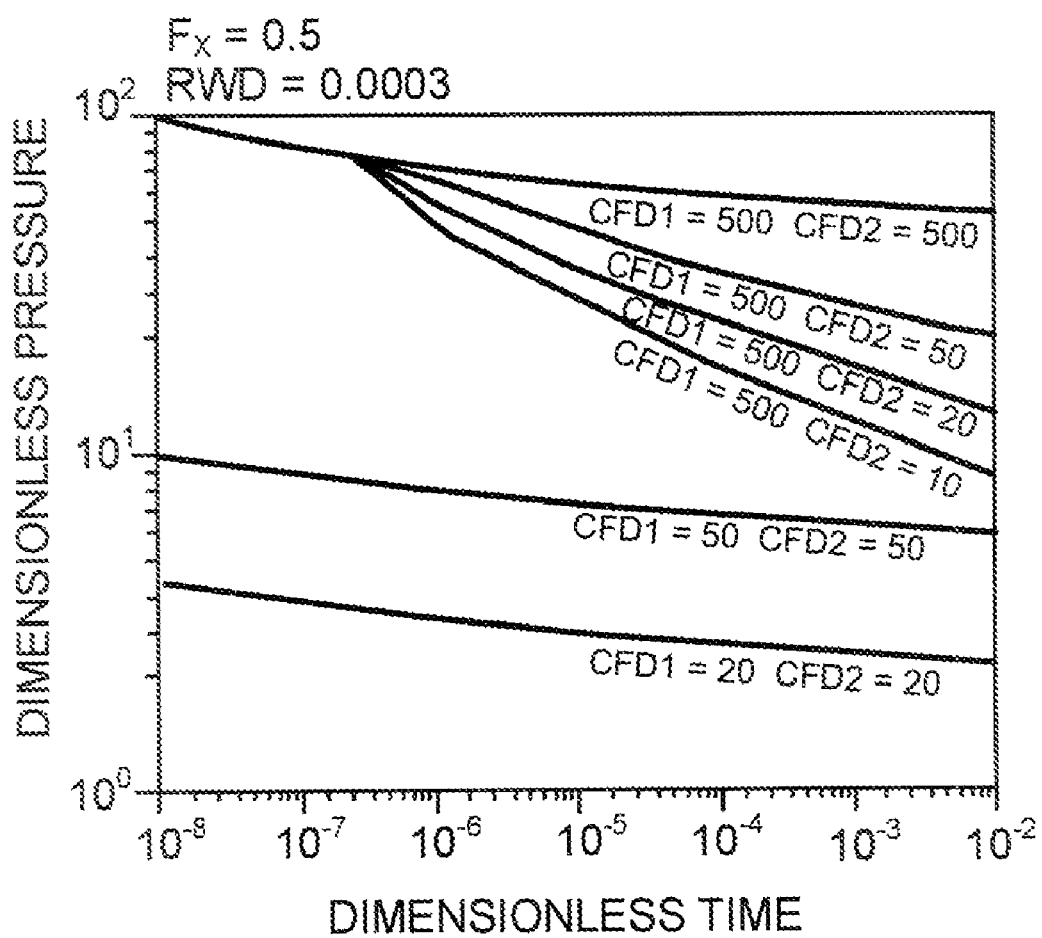
FIG. 16 is a graph showing an effect of tail-in on well productivity.

Reservoir heterogeneity and directional permeability also affect the optimum number of fractures. The effect of directional permeability on the optimum number of fractures is investigated with the simulator by varying the ratio of horizontal permeabilities. FIG. 16 shows the results of cumulative production vs. the number of fractures at 6 and 24 months as a function if directional permeability. The two permeabilities considered are horizontal, with $k_x$ being the permeability parallel to the fracture plane (perpendicular to the horizontal wellbore axis) and $k_y$ being perpendicular to $k_x$. The $k_x/k_y=1.0$ curves in FIG. 16 are the same as those in FIG. 15, and they show five fractures as optimum. When $k_x<k_y$, few fractures are needed to produce the reservoir. This is demonstrated for the case with $k_x/k_y=0.10$, which results in three fractures being optimum. When $k_y<k_x$, the optimum number of fractures increases. In fact, for the case shown in FIG. 16 ($k_x/k_y=10$), the optimum number of fracture is >10; economics would dictate this optimum number of fractures.

Consideration of directional permeability simulates the presence of oriented natural fractures. Thus, it is imperative that the presence and direction of natural fractures be established so that orientation of the horizontal wellbore and induced fractures with respect to the natural fractures can be planned to maximize production from the reservoir.

Optimization, in a strict sense, definitely requires the consideration of economic factors, including the cost of a fracturing treatment, the price of produced hydrocarbon, and the production cost. This strict optimization may be achieved by studying parameters such as the net present value and the benefit/cost ratio.

We use a loose definition of optimization here. The optimum number of fractures is the number of fractures at which the rate of increased productivity diminishes.

Optimization of Horizontal Well Location. This section presents a technique to optimize the placement of the horizontal section of a well. The horizontal placement is designed to give optimum fracture height.

A horizontal well location in a given field may be investigated so that future fracturing treatment would expose most of the formation. Analysis may be performed by assuming that vertical fracture growth is controlled by the variation in the closure stress gradient. The main treatment parameter that could offset this containment criterion is the treatment pressure. Theoretically, the limits of the treatment pressure to achieve certain fracture growth can be determined. A 2D analysis for fracture extension in a three-layered system was extended for continuous stress change. By placing the horizontal well along various locations in the formation and by calculating the total fracture height for a certain treatment pressure, we can determine the optimum location of the well to yield maximum exposure of the pay zone. Derivation of the equation is presented in Appendix C.

Optimization Example. An actual well was logged between 4,480 and 4,639 ft, giving stresses every 10 ft. Generated data are presented in Table 2.

TABLE 2

Summary of Stress Data

| Location | Top (ft) | Bottom (ft) | Stress (psia) |
|---|---|---|---|
| Pay Zone 1 | 3,500 | 4,480 | 2,664.1 |
| | 4,480 | 4,490 | 2,601.1 |
| | 4,490 | 4,500 | 2,625.1 |
| | 4,500 | 4,510 | 2,144.1 |
| | 4,510 | 4,520 | 2,348.1 |
| | 4,520 | 4,530 | 2.416.1 |
| | 4,530 | 4,540 | 2,594.1 |
| | 4,540 | 4,550 | 2,273.1 |
| Shale | 4,550 | 4,560 | 3,070.2 |
| | 4,560 | 4,570 | 2,876.2 |
| | 4,570 | 4,580 | 3,330.2 |
| | 4,580 | 4,590 | 3,448.2 |
| | 4,590 | 4,600 | 3,244.2 |
| | 4,600 | 4,610 | 3,196.2 |
| Pay Zone 2 | 4,610 | 4,620 | 2,438.2 |
| | 4,620 | 4,630 | 2,544.3 |
| | 4,630 | 5,000 | 3,253.3 |

A simulated fracture is initiated and propagated from the center of each zone toward the outer layers in 2.5-ft steps. To accomplish this propagation, the required fracture pressure is calculated with the technique described in Appendix C. The total fracture heights (pay-zone height plus fracture growth into the upper and lower zones), which correspond to $\Delta p=250$ psi [(bottom-hole treatment pressure) minus closure stress] are compared in FIG. 17.

Figure 17:
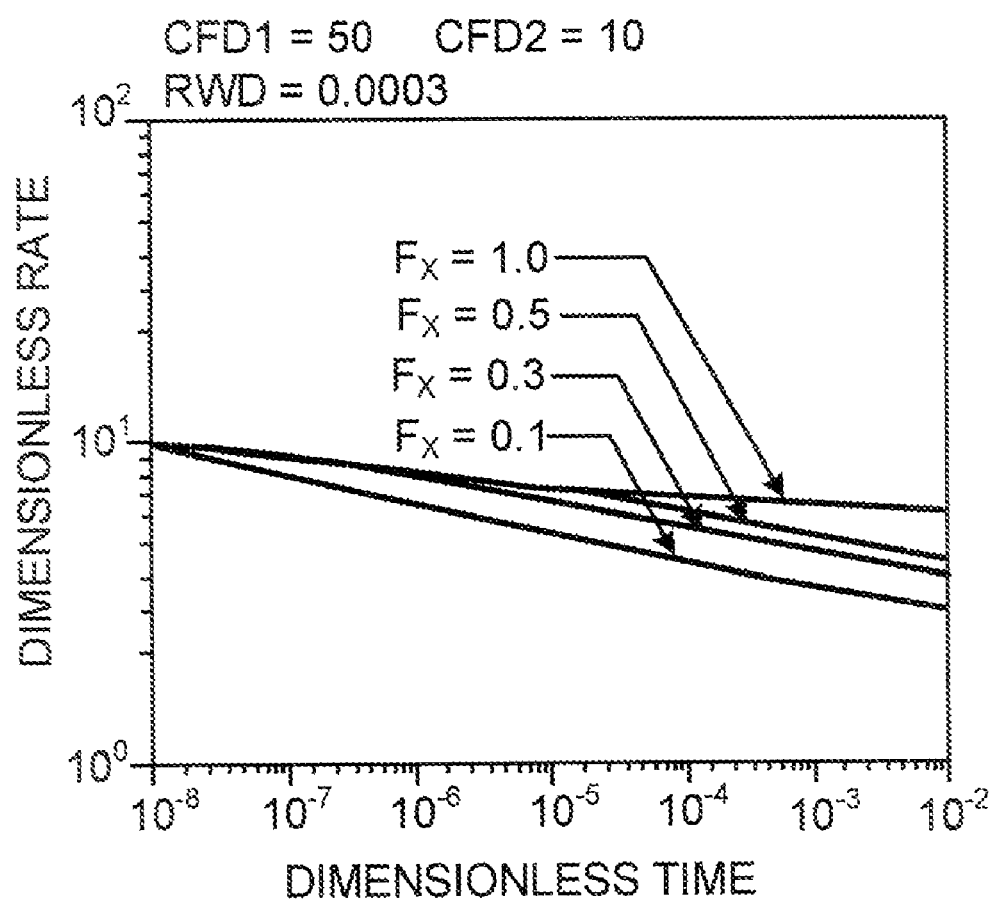
FIG. 17 is a graph showing an effect of tail-in radius on well productivity.
Figure 18:
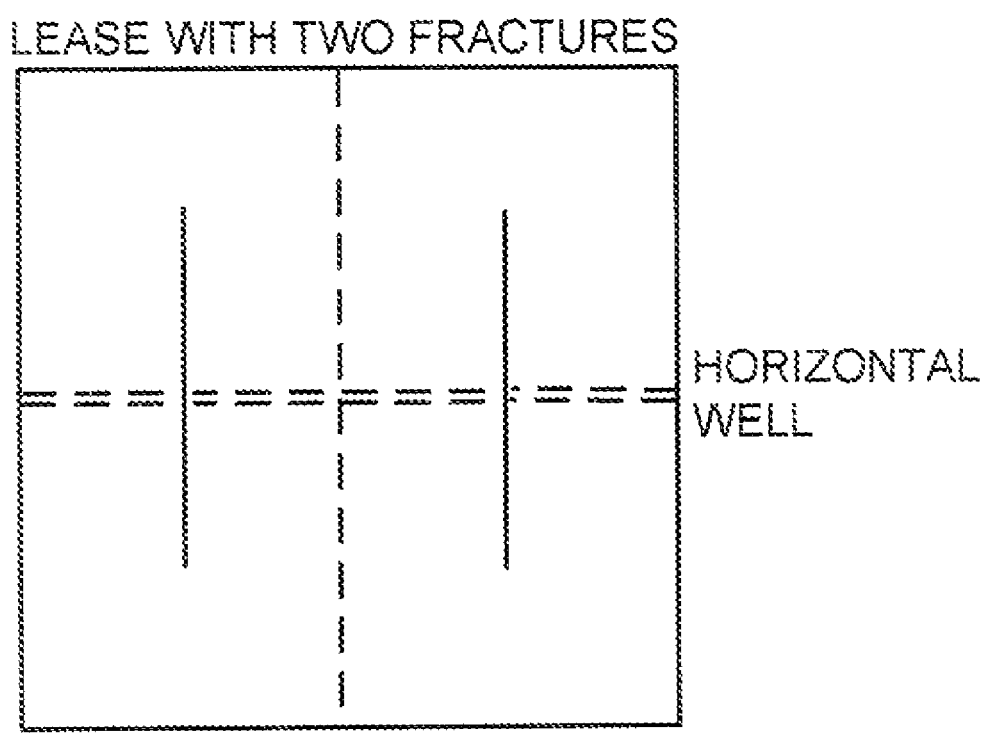
FIG. 18 is a plan view schematic of a two-dimensional simulator run for a case of two fractures in a horizontal well.
Figure 19:
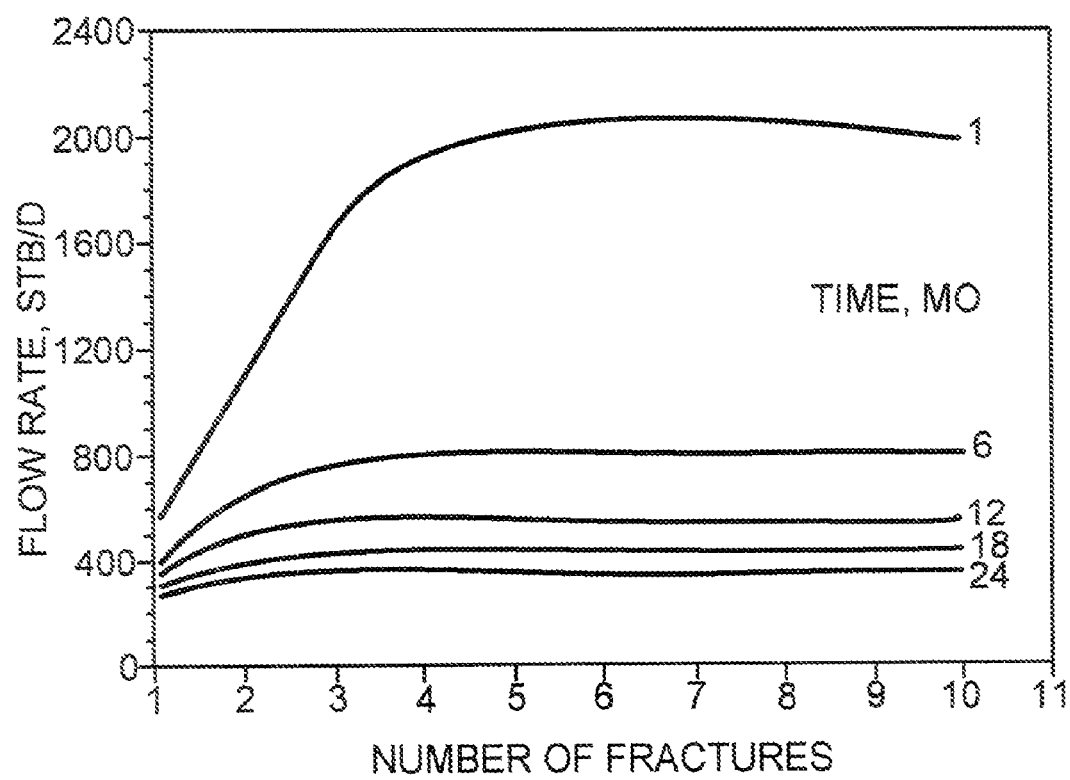
FIG. 19 is a graph showing system flow rate versus number of fractures.
Figure 20:
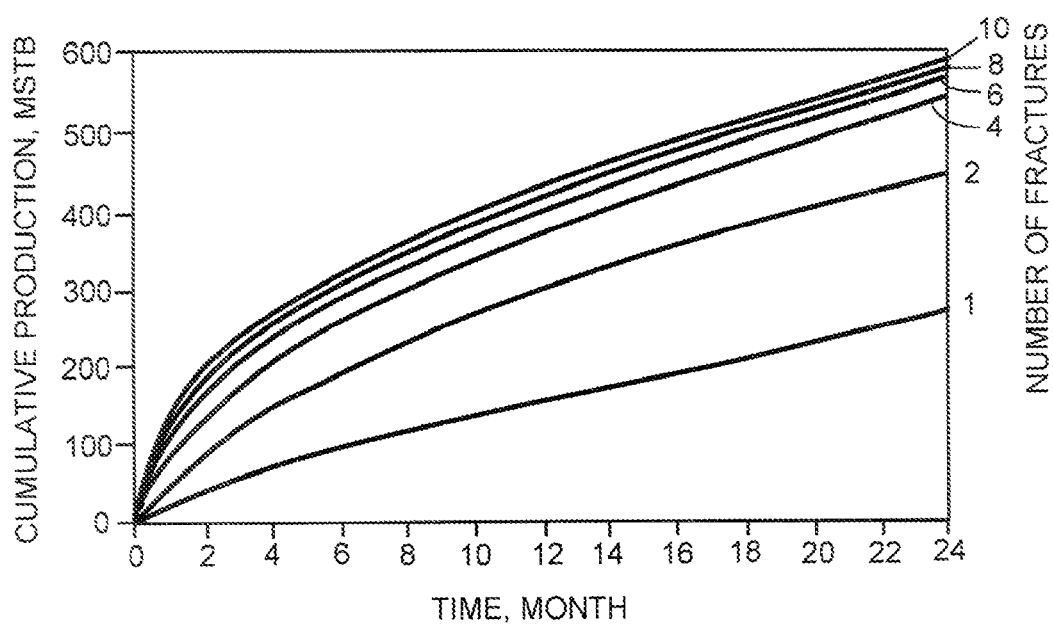
FIG. 20 is a graph showing cumulative production versus time.
Figure 21:
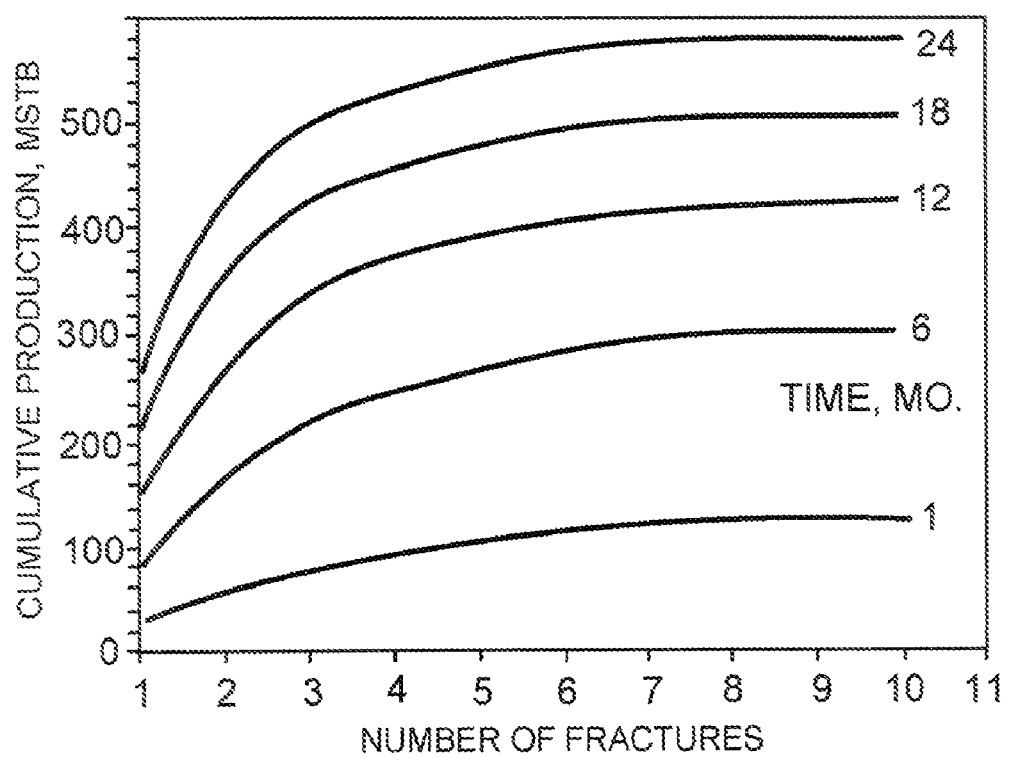
FIG. 21 is a graph showing cumulative production versus number of fractures.
Figure 22:
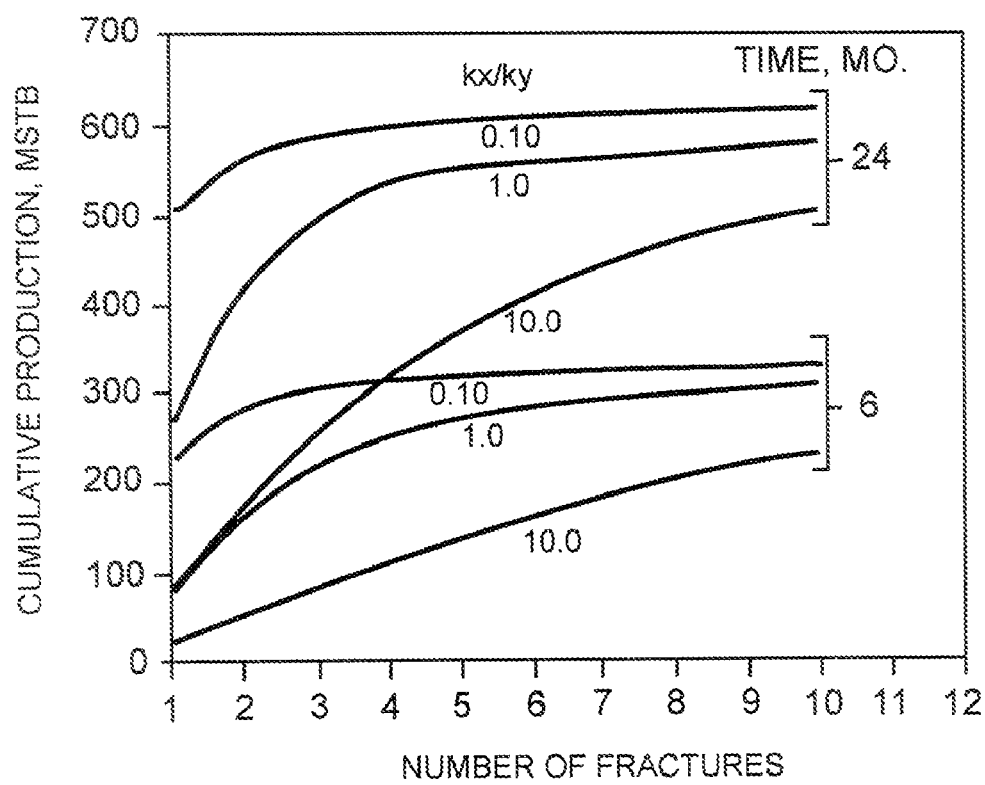
FIG. 22 is a graph showing cumulative production versus number of fractures for the effect of directional horizontal permeabilities.
Figure 23:
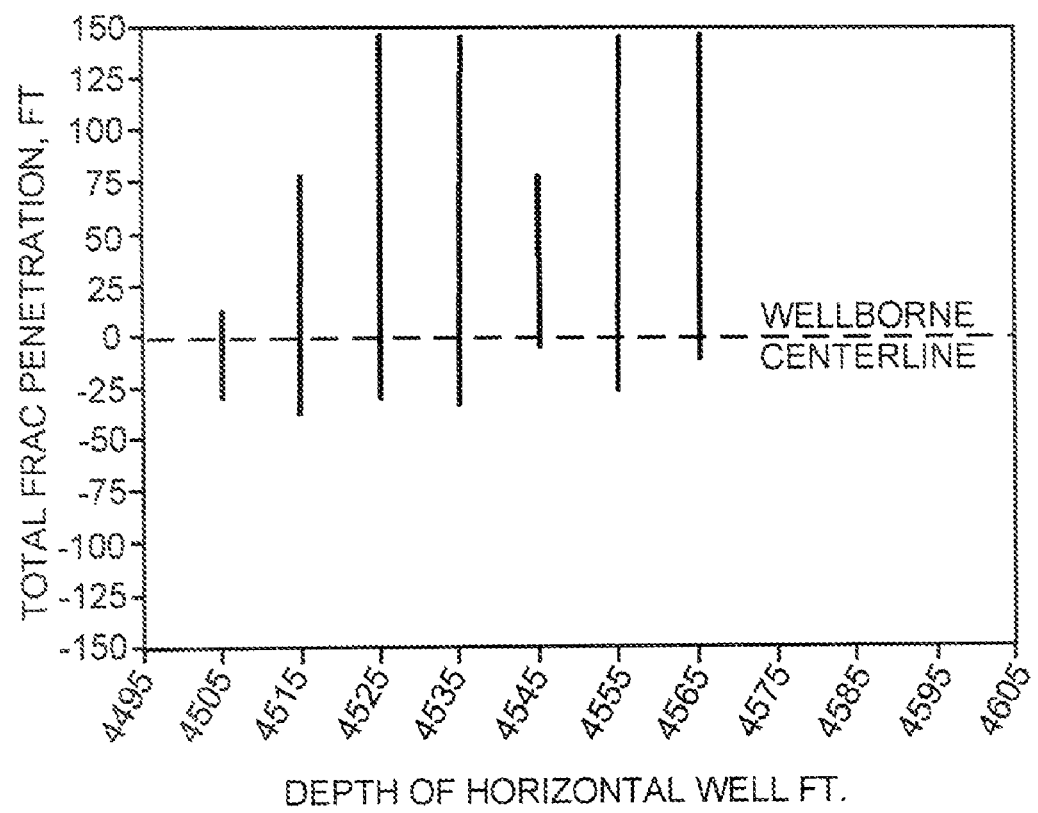
FIG. 23 is a graph showing a prediction of total fracture height as initiated from various depths based on a $\Delta p=250$ psi.

The x axis in FIG. 17 represents the depth of the horizontal well or the depth of fracture initiation. The y axis gives the amount of fracture penetration into the upper and lower layers from the horizontal well's center (dotted) line. for example, a fracture initiated from a well drilled at 4,505 ft would penetrate 10 ft above and 30 ft below the wellbore, creating a total height of 40 ft at a pressure of 2,400 psi. As seen from the comparison, a fracture created from a horizontal well drilled at 4,545 ft would propagate upward in the upper pay zone with very little penetration in the lower zones. This conclusion would not be critically changed at a reference $\Delta p \neq 250$ psi. The magnitudes of fracture penetration, however, will be greater; e.g., for $\Delta p=800$ psi, a fracture from 4,545 ft will penetrate 40 ft, instead of 5 ft, into the lower layers and more that 150 ft upward, compared to 70 ft at 250 psi.

Conclusions. If a horizontal well is drilled parallel to the minimum horizontal stress, multiple fractures may be created. Because of the convergence of streamlines inside the fracture toward the wellbore, we would expect to observe a higher pressure drop than is usually observed in a vertical well intercepting a vertical fracture with similar conductivity. Consequently, a very high $C_{fD}$ may be necessary. A tail-in with high conductivity will definitely help to reduce the observed pressure drop. Fracturing-fluid-cleanup considerations dictate high conductivity.

If high or essentially infinite conductivity is feasible, an optimum number of fractures may be obtained. This optimum number depends on formation and fluid properties and on the presence of natural fractures.

With the in-situ stress varying through the pay zone, optimum placement of the horizontal wellbore can be determined. Optimum placement is based on the created fracture's height.

NOMENCLATURE a=variable defined by Eq. A-26
A=area, acres
B=FVF, RB/STB
$c_{ft}$=total fracture compressibility, $psi^{-1}$
$c_t$=total system compressibility, $psi^{-1}$
$C=K_{IC}\sqrt{\pi}[(1/\sqrt{h_t})-(1/\sqrt{h_j})]$
$C_f$=fracture conductivity, md·ft
$C_{fD}$=dimensionless fracture conductivity
$C_1, C_2, C_3$=variables in Laplace space
D=fracture spacing, ft
$F_x$=ratio of tail-in length to total fracture length
$F(y,h_t)$=rock properties function
h=formation thickness, ft
$h_j$=thickness of jth layer with $\sigma_j$, ft
$h_t$=total fracture length, ft
$I_0$=modified Bessel function of first kind, zero order
$I_1$=modified Bessel function of first kind, first order
k=formation permeability, md
$k_f$=fracture permeability, md
$k_x, k_y$=directional horizontal permeabilities, md
$K_f$=stress intensity factor, psi-$\sqrt{in.}$
$K_{IC}$=fracture toughness, psi-$\sqrt{in.}$
$K_0$=modified Bessel function of second kind, zero order
$K_1$=modified Bessel function of second kind, first order
L=variable defined by Eq. A-27
$L_n$=variable defined by Eq. A-24
p=formation pressure, psi
$P_f$=fracture pressure, psi
$P_h$=hydrostatic pressure caused by fluid density, psi
$p_i$=initial pressure, psi
$P_{wD}$=dimensionless wellbore pressure
$P_{wf}$=flowing wellbore pressure, psi
$\Delta p$=pressure difference, psi
q=well flow rate, STB/D
r=radius, ft
$r_w$=wellbore radius, ft
s=Laplace transform variable
$S_w$=water saturation, percent
t=flowing time, hours
$t_D$=dimensionless time
$T_{bh}$=bottomhole temperature, °F.
w=fracture width, ft
$x_f$=fracture half-length, ft
$x_f'$=length of tail-in, ft x,y=space coordinates, ft
η=formation hydraulic diffusivity, and psi/cp
$\eta_f$=ratio of fracture/formation hydraulic diffusivity
μ=fluid viscosity, cp
$\sigma_{Hmax}$=maximum horizontal stress, psi
$\sigma_{Hmin}$=minimum horizontal stress, psi
$\sigma_j$=closure stress at initiation zone, psi
$\sigma_n$=closure stress at fracture tip, psi
$\Delta\sigma=\sigma_n-\sigma_j$, psi
$\Delta\sigma_j$=difference in stress between adjacent layers, psi
φ=formation porosity, fraction
$\phi_f$=fracture porosity, fraction Subscripts
D=dimensionless
i=initial
j=layer
t=total
1=tail-in
2=fracture minus tail-in Superscript
~=Laplace transform

REFERENCES

1. Giger, F. M., Reiss, L. H., and Jourdan, A. P.: "The Reservoir Engineering Aspects of Horizontal Drilling," paper SPE 13024 presented at the 1984 SPE Annual Technical Conference and Exhibition, Houston, September. 16-19.
2. Joshi, S. D.: "A Review of Horizontal Well and Drainhole Technology," paper SPE 16868 presented at the 1987 SPE Annual Technical Conference and Exhibition, Dallas, September. 27-30.
3. Ertekin, T., Sung, W., and Schwerer, F. C.: "Production Performance Analysis of Horizontal Drainage Wells for the Degasification of Coal Seams," JPT (May 1988) 625-32.
4. Giger, F. M.: "Low-Permeability Reservoir Development Using Horizontal Wells," paper SPE 16406 presented at the 1987 SPE/DOE Low Permeability Reservoirs Symposium, Denver, May 18-19.
5. Joshi, S. D.: "Augmentation of Well Productivity With Slant and Horizontal Wells,": JPT (June 1988) 729-39; Trans., AIME, 285.
6. Clonts, M. D. and Ramey, H. J. Jr.: "Pressure-Transient Analysis for Wells With Horizontal Drainholes," paper SPE 15116 presented at the 1986 SPE California Regional Meeting, Oakland, April 2-4.
7. Ozkan, E., Raghavan, R., and Joshi, S. D.: "Horizontal-Well Pressure Analysis," SPEFE (December 1989) 567-75; Trans., AIME, 287.
8. Daviau, F. et al.: "Pressure Analysis for Horizontal Wells," SPEFE (December 1988) 716-24.
9. Goode, P. A. and Thambynayagam, R. K. M.: "Pressure Drawdown and Buildup Analysis of Horizontal Wells in Anisotropic Media," SPEFE (December 1987) 683-97; Trans., AIME, 283.
10. Karcher, B. J., Giger, F. M., and Combe, J.: "Some Practical Formulas To Predict Horizontal Well Behavior," paper SPE 15430 presented at the 1986 SPE Annual Technical Conference and Exhibition, New Orleans, Oct. 5-8.
11. Hsiao, C.: "A Study of Horizontal-Wellbore Failure," SPEPE (November 1988) 489-94.
12. Daneshy, A. A. et al.: "In-Situ Stress Measurements During Drilling," JPT (Aug. 1986) 891-98; Trans., AIME, 281.
13. El Rabaa, A. W. M. and Meadows, D. L.: "Laboratory and Field Applications of the Strain Relaxation Method," paper SPE 15072 presented at the 1986 SPE California Regional Meeting, Oakland, April 2-4.

14. Cinco-Ley, H. and Samaniego-V., F.: "Transient Pressure Analysis for Fractured Wells," JPT (September 1981) 1749-66.
15. Schulte, W. M.: "Production From a Fractured Well With Well Inflow Limited to Part of the Fracture Height," SPEPE (September 1986) 333-43.
16. Soliman, M. Y.: "Design and Analysis of a Fracture With Changing Conductivity," J. Cdn. Pet. Tech. (September.-October 1986) 62-67).
17. Stehfest, H.: "Algorithm 368: Numerical Inversion of Laplace Transforms," Communications of the ACM, D-5 (January 1970) 13, No. 1, 47-49.
18. Soliman, M. Y. and Hunt, J. L.: "Effect of Fracturing Fluid and Its Cleanup on Well Performance," paper SPE 14514 presented at the 1985 SPE Eastern Regional Meeting, Morgantown, Nov. 6-8.
19. Soliman, M. Y.: "Fracture Conductivity Distribution Studied," Oil & Gas J. (Feb. 10, 1986) 89-93.
20. Bennett, C. O. et al.: "Influence of Fracture Heterogeneity and Wing Length on the Response of Vertically Fractured Wells," SPEJ (April 1983) 219-30.
21. Soliman, M. Y., Venditto, J. J., and Slusher, G. L.: "Evaluating Fractured Well Performance by Use of Type Curves," paper SPE 12598 presented at the 1984 SPE Permian Basin Oil & Gas Recovery Conference, Midland, March 8-9.
22. Rice, J. R.: "Mathematical Analysis in the Mechanics of Fracture," Treatise on Fracture, Academic Press Inc., New York City (1962) 2, Chap. 3, 191-276.

APPENDIX A

Solution for Constant-Rate Case

If flow within the fracture is assumed to be radial, the pressure behavior is described by $$\frac{\partial^2 p_{fD1}}{\partial r_D^2} + \frac{1}{r_D}\frac{\partial p_{fD1}}{\partial r_D} + \frac{2}{C_{fD1}}\frac{\partial p_D}{\partial y_D}\bigg|_{y_D=0} = \frac{1}{\eta}\frac{\partial p_{fD1}}{\partial t_D}, \quad (A-1)$$

where $0 \leq r_D \leq F_x, t_D > 0$, and $$\frac{\partial^2 p_{fD2}}{\partial r_D^2} + \frac{1}{r_D}\frac{\partial p_{fD2}}{\partial r_D} + \frac{2}{C_{fD1}}\frac{\partial p_D}{\partial y_D}\bigg|_{y_D=0} = \frac{1}{\eta}\frac{\partial p_{fD2}}{\partial t_D}, \quad (A-2)$$

where $F_x \leq r_D \leq \infty, t_D > 0$.

The initial condition is $$p_{fD1} = p_{fD2} = 0. \quad (A-3)$$

Boundary conditions are $$\frac{\partial p_{fD1}}{\partial r_D} = -\frac{1}{C_{fD}r_{wD}}, \quad r_D = r_{wD}, \quad (A-4)$$

$$p_{fD1} = p_{fD2}, \quad r_D = F_x, \quad (A-5)$$

$$C_{fD1}\frac{\partial p_{fD1}}{\partial r_D} = C_{fD2}\frac{\partial p_{fD2}}{\partial r_D}, \quad r_D = F_x, \quad (A-6)$$

Eqs. A-5 and A-6 ensure the continuous change of pressure and rate inside the fracture at the point where the fracture conductivity changes.

Transient flow in the formation is described by $$\frac{\partial^2 p_D}{\partial y_{D2}} = \frac{\partial p_D}{\partial t_D}, \quad 0 < y_D < \infty, t_D > 0, \quad (A-8)$$

with initial conditions of (A-9)

$$p_D = 0, \quad 0 < y_D < \infty, t_D = 0,$$

and boundary conditions (A-10)

$$p_D = p_{fD}, \quad y_D = 0, t_D > 0,$$

Eq. A-10 indicates that formation pressure should be equal to fracture pressure at points of contact. Definitions in Eqs. A-12 and A-13 use formation permeability to achieve the dimensionless form given in Eq. A-1.

$$t_D = 0.000264 kt/\phi \mu c_1 x_f^2, \quad (A-14)$$

$$r_D = r/x_f, \quad (A-15)$$

$$r_{wD} = r_w/x_f, \quad (A-16)$$

$$F_x = x_f'/x_f, \quad (A-17)$$

$$C_{fD} = k_f w/k x_f, \quad (A-18)$$

and $\eta_f = k_f \phi c_1 / k \phi_f c_{f1}, \quad (A-19)$

The three partial differential equations (Esq. A-1, A-2, and A-8) are coupled with the boundary conditions. By Laplace transform and by algebraic substitution, the system of equations is reduced to a system of ordinary differentia equations.

The final expression for the Laplace transform of dimensionless pressure at the wellbore is $$\tilde{p}_{wD} = C_1[C_2 I_0(r_{wD}L_1) + K_0(r_{wD}L_1)], \quad (A-20)$$

$$\tilde{p}_{wD} = C_1[C_2 I_0(r_{wD}L_1) + K_0(r_{wD}L_1)], \quad (A-20)$$

where $C_1 = \dfrac{-1}{3 C_{fD} r_{wD} L_1 [C_2 I_1(r_{wD}L_1) - K_1(r_{wD}L_1)]}, \quad (A-21)$ $$C_2 = \frac{C_3 K_1(F_x L_1) - K_0(F_x L_1)}{I_0(F_x L_1) + C_3 I_1(F_x L_1)}, \quad (A-22)$$

$$C_3 = \frac{C_{fD1}}{C_{fD2}} \frac{L_1}{L_2} \frac{K_0(F_x L_2)}{K_1(F_x L_2)}, \quad (A-23)$$

$$L_n = \left[(2\sqrt{s}/C_{fDn}) + (s/\eta_{fDn})\right]^{1/2}. \quad (A-24)$$

The solution for a uniform fracture may be derived from Eq. A-20 by setting $F_x = 1.0$. Eq. A-25 describes the final solution for a uniform-conductivity fracture.

$$\tilde{p}_{wD} = \frac{K_0(r_{wD}L)}{s C_{fD} L K_1(r_{wD}L) r_{wD}} \quad (A-25)$$

Eq. A-25 is somewhat different from Schulte's[15] Eq. A-8, which has a typographical error. It should √a have the term in its denominator. Also, Schulte's equation was for a half circle; consequently, the calculated pressure drop from his equation would be twice the pressure drop calculated with the equation for a full circle at the same production rate. Schulte also ignored the storativity of the fracture; consequently, a in his paper is defined as $$a=2\sqrt{s}/C_{fD}, \quad \text{(A-26)}$$

In this paper, L2, which is equivalent to α, is defined as $$L^2=(2\sqrt{s}/C_{fD})+(s/\eta_{fD}), \quad \text{(A-27)}$$

The solution developed here is basically for early-time producing a radial/linear flow regime comparable to the bilinear flow regime in vertical wells.[14] Consequently, only formation permeability perpendicular to fracture affects fluid flow. After a long producing time, permeability both parallel and perpendicular to fracture will affect fluid flow.

APPENDIX B

Solution of Constant-Pressure Case

The procedure presented above can also be used to solve equations for flow under constant wellbore pressure. Slight modifications, however, are required. First, the dimensionless pressure is defined as $$P_D=(P_i-p)/(P_i-P_{wf}) \quad \text{(B-1)}$$

and $P_{fD}=(P_i-P_f)/(P_i-P_{wf})$ (B-2)

The boundary condition at the wellbore is replaced by $$P_{fD}=1.0, \quad \text{(B-3)}$$

and the dimensionless flow rate is $$q_D = -C_{fD}\frac{\partial p_{fD}}{\partial r_D}r_{wD} \quad \text{(B-4)}$$

With these definitions, the governing partial differential equations can be solved for a changing-conductivity fracture, as presented in Eq. B-5.

$$\tilde{q}_D=-C_{fD1}C_1L_1[C_2I_1(r_{wD}L_1)-K_1(r_{wD}L_1)]r_{wD}, \quad \text{(B-5)}$$

where $C_1=1/\{[C_2I_0(L_1)+K_0(L_1)]\}$ (B-6)

$$C_2 = \frac{C_3K_1(F_xL_1) - K_0(F_xL_1)}{I_0(F_xL_1) - C_3I_1(F_xL_1)}, \text{ and} \quad \text{(B-7)}$$

$$C_3 = \frac{C_{fD1}}{C_{fD2}}\frac{L_1}{L_2}\frac{K_0(F_xL_2)}{K_1(F_xL_2)}. \quad \text{(B-8)}$$

The solution for a uniform fracture can be obtained from Eqs. B-5 through B-8 by setting $F_x=1$, which yields the following final form:

$$\tilde{q}_D = \frac{C_{fD}LK_1(r_{wD}L)}{sK_0(r_{wD}L)}r_{wD} \quad \text{(B-9)}$$

APPENDIX C

Calculating Fracture Pressure for Propagation

The relationship between the total fracture height, the surrounding stresses, and the pressure inside the fracture is found by manipulating Rice's equation[22]:

$$K_I = C\int_{-h_i}^{h_i} p(y)F(y, h_i)\,dy, \quad \text{(C-1)}$$

where $K_1$ is the stress intensity factor at the tips of a fracture, $h_t$, loaded by inside pressure $p(y)$. For more than three layers, the solution can be written in the form:

$$\Delta p = C + \Delta\sigma - 1/\pi\sum_{j=1}^{n}\Delta\sigma_j \times \sin^{-1}(h_j/h_t) + p_h. \quad \text{(C-2)}$$

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A method comprising:
    collecting data from a fracture treatment, the fracture treatment fracturing a reservoir by injecting fluid into the reservoir through a well;
    determining a flow regime from the fracture treatment by analyzing the collected data for a presence of a plurality of different flow regimes, the plurality of different flow regimes comprising at least two of a pseudo-radial flow regime, a bilinear flow regime, or a linear flow regime, the pseudo-radial flow regime comprising converging streamlines, the linear flow regime comprising parallel stream lines, and the bi-linear flow regime comprising a first set of parallel stream lines and a second set of parallel stream lines perpendicular to the first set; and
    performing a subsequent fracture treatment, the subsequent fracture treatment based on properties determined using the flow regime.

2. The method of claim 1, wherein the data comprises pressure data from the fracture treatment.

3. The method of claim 1, wherein the data comprises post-closure data from the fracture treatment.

4. The method of claim 1, wherein the data comprises pressure data and determining the flow regime from the fracture treatment comprises:
    plotting pressure data during a post-closure period of the fracture treatment to generate a plot; and
    determining the flow regime from the plot.

5. The method of claim 1, further comprising determining formation properties based on the flow regime and the data.

6. The method of claim 1, wherein determining a flow regime from the fracture treatment by analyzing the collected data for a presence of a plurality of different flow regimes comprises:
    determining a first value of a slope in a plot representing the collected data, wherein the plurality of different flow regimes correspond to a plurality of different values of the slope; and
    determining the flow regime from the first value of the slope.

7. The method of claim 4, wherein determining the flow regime comprises determining the flow regime from a slope of the plot.

8. The method of claim 5, wherein determining the formation properties comprises determining at least one of a formation permeability k, an initial reservoir pressure $p_i$, a fracture conductivity $k_f$, or a fracture half length $L_f$.

9. The method of claim 5, wherein determining the formation properties comprises determining at least one of the formation properties based at least in part on a sum of a pumping time $t_p$ and a shut-in time $\Delta t$.

10. The method of claim 5, wherein determining the formation properties comprises determining the formation properties based at least in part on an intercept ($b_r$) in a logarithmic plot of a pressure versus a time.

11. The method of claim 5, wherein determining the formation properties comprises determining a formation permeability k based at least in part on parameters including an injected volume V, a viscosity, $\mu$, an intercept $b_r$ in a logarithmic plot of a pressure versus a time, and net pay thickness h.

12. The method of claim 5, wherein determining the formation properties comprises:
    selecting one or more equations that are appropriate for the flow regime; and
    using the data and the one or more equations to determine the formation properties.

13. The method of claim 7, wherein the pressure data is plotted on logarithmic-logarithmic graph.

14. The method of claim 13, wherein the logarithmic-logarithmic graph comprises a plot of a derivative of a pressure with respect to a time versus a total time of the fracture treatment.

15. A method for enhancing a fracture treatment, comprising:
    performing an initial fracture treatment, the fracture treatment fracturing a reservoir by injecting fluid into the reservoir through a well;
    collecting data from the fracture treatment, the data comprising pressure data from a post-closure period of the fracture treatment;
    determining a flow regime from the fracture treatment by analyzing the collected data for a presence of a plurality of different flow regimes, determining the flow regime comprises:
        generating a plot on a logarithmic-logarithmic graph of the pressure data from the post-closure period, the plot including a plot of a derivative of a pressure with respect to a time versus a total time of the fracture treatment, the derivative of the pressure with respect to the time comprising $$t\frac{\partial p_{fo}}{\partial t};$$

and
        determining the flow regime from a slope of the plot;
    determining formation properties for the well based on the flow regime;
    designing a subsequent fracture treatment for the well based on the formation properties; and
    performing the subsequent fracture treatment.

16. The method of claim 15, wherein the plurality of different flow regimes comprise at least two of a pseudo-radial flow regime, a bilinear flow regime, or a linear flow regime.

17. The method of claim 15, wherein the data comprises pressure data and determining the flow regime from the fracture treatment comprises
    plotting the pressure data during the post-closure period of the fracture treatment to generate the plot.

18. An article of manufacture comprising machine-readable media storing instructions for causing one or more processors to:
    collect post-closure data from a fracture treatment, the fracture treatment fracturing a reservoir by injecting fluid into the reservoir through a well;
    determine a flow regime from the fracture treatment by analyzing the collected post-closure data for a presence of a plurality of different flow regimes, the plurality of different flow regimes comprising at least two of a pseudo-radial flow regime, a bilinear flow regime, or a linear flow regime, the pseudo-radial flow regime comprising converging streamlines, the linear flow regime comprising parallel stream lines, and the bi-linear flow regime comprising a first set of parallel stream lines and a second set of parallel stream lines perpendicular to the first set; and
    output the flow regime.

19. The article of manufacture of claim 18, further comprising instructions for causing the one or more processors to plot the post-closure data on a logarithmic-logarithmic graph and to determine the flow regime based on the plot.

20. The article of manufacture of claim 18, wherein the data comprises post-closure data.

21. The article of manufacture of claim 19, wherein the flow regime for the fracture treatment is determined based on a slope of the plot.

22. The article of manufacture of claim 18, further comprising instructions for causing the one or more processors to determine formation properties based on the flow regime and the data.

23. The article of manufacture of claim 21, wherein the logarithmic-logarithmic graph comprises a plot of a derivative of a pressure with respect to a time versus a total time of the fracture treatment.

24. A system comprising:
    data collected from a fracture treatment, the fracture treatment fracturing a reservoir by injecting fluid into the reservoir through a well;
    means for determining a flow regime from the fracture treatment by analyzing the collected data for a presence of a plurality of different flow regimes, the plurality of different flow regimes comprising at least two of a pseudo-radial flow regime, a bilinear flow regime, or a linear flow regime, the pseudo-radial flow regime comprising converging streamlines, the linear flow regime comprising parallel stream lines, and the bi-linear flow regime comprising a first set of parallel stream lines and a second set of parallel stream lines perpendicular to the first set; and
    means for outputting the flow regime.

25. The system of claim 24, further comprising means for determining formation properties based on the flow regime and the data.

26. A method for determining properties of a formation, comprising:
    performing a fracture treatment, the fracture treatment fracturing a formation by injecting fluid into the formation through a well;
    collecting post-closure pressure data from the fracture treatment;

plotting a derivative of the post-closure pressure data on a logarithmic-logarithmic graph, the derivative of the post-closure pressure data comprising $$t\frac{\partial p_{fo}}{\partial t};$$

determining a slope of the plot;
determining a presence of one of a pseudo-radial or bilinear flow regime of the fracture treatment based on the slope of the plot;

determining formation properties based on the flow regime; and
providing the formation properties to at least one of a data collection unit or a person.

27. The method of claim 26, wherein the flow regime comprises one of a pseudo-radial flow regime, a bilinear flow regime, or a linear flow regime.

* * * * *